(12) United States Patent
Esashi et al.

(10) Patent No.: US 7,223,329 B2
(45) Date of Patent: May 29, 2007

(54) ACTIVE SLENDER TUBES AND METHOD OF MAKING THE SAME

(76) Inventors: Masayoshi Esashi, 11-9, Yagiyamaminami, 1-chome, Taihaku-ku, Sendai-shi, Miyagi-ken, 982-0807 (JP); Yoichi Haga, 6-22-1003, Ichibancho, 1-chome, Aoba-ku, Sendai-shi, Miyagi-ken, 980-0811 (JP)

(*) Notice: Subject to any disclaimer, the term of this patent is extended or adjusted under 35 U.S.C. 154(b) by 542 days.

(21) Appl. No.: 10/703,445

(22) Filed: Nov. 10, 2003

(65) Prior Publication Data

US 2005/0006009 A1 Jan. 13, 2005

Related U.S. Application Data

(62) Division of application No. 09/457,294, filed on Dec. 9, 1999, now Pat. No. 6,672,338.

(30) Foreign Application Priority Data

Dec. 14, 1998 (JP) ............................. 10-355170
Sep. 27, 1999 (JP) ............................. 11-273317

(51) Int. Cl.
*C25D 5/02* (2006.01)
*A61M 29/00* (2006.01)
*A61M 5/00* (2006.01)

(52) U.S. Cl. .................. 205/114; 606/108; 606/192; 606/194; 604/8; 128/897

(58) Field of Classification Search ................ 205/114; 606/108, 192, 194; 604/8; 128/897
See application file for complete search history.

(56) References Cited

U.S. PATENT DOCUMENTS 4,748,969 A 6/1988 Wardle
4,753,223 A 6/1988 Bremer
4,790,624 A 12/1988 Van Hoye et al.
4,846,573 A 7/1989 Taylor et al.
4,930,494 A 6/1990 Takehana et al.
5,179,934 A 1/1993 Nagayoshi et al.

(Continued)

FOREIGN PATENT DOCUMENTS

JP 59-097115 6/1984

(Continued)

*Primary Examiner*—Roy V. King
*Assistant Examiner*—Nicholas A Smith
(74) *Attorney, Agent, or Firm*—Westerman, Hattori, Daniels & Adrian, LLP.

(57) ABSTRACT

A method of making an active slender tube as implemented as a catheter, guide wire, or any other medical or non-medical micro-mechanical or -system or system's active micro-component is disclosed, comprising preparing an actuator made from a shape memory alloy (SMA) and forming at least a portion of a tubular body; disposing outside of SMA made actuator an elastically deformable outer skeleton coaxially therewith; and fastening together SMA made actuator and outer skeleton wire adjacent to non-insulated portions, step of fastening includes a step of passing an electric current through a lead wire while in an electroplating liquid to deposit a metal on lead wire and non-insulated portions from said liquid and thereby to electrically join SMA made actuator and outer skeleton together at corresponding areas.

9 Claims, 25 Drawing Sheets

~~~NH+: acrylic resin of cation type dispersed in water [charged positively]

U.S. PATENT DOCUMENTS

| | | |
|---|---|---|
| 5,220,911 A | 6/1993 | Tamura |
| 5,271,382 A | 12/1993 | Chikama |
| 5,449,021 A | 9/1995 | Chikama |
| 5,472,017 A | 12/1995 | Kovalcheck |
| 5,482,029 A | 1/1996 | Sekiguchi et al. |
| 5,531,685 A | 7/1996 | Hemmer et al. |
| 5,577,992 A | 11/1996 | Chiba et al. |
| 5,763,979 A | 6/1998 | Mukherjee et al. |
| 5,833,632 A | 11/1998 | Jacobson et al. |
| 5,860,914 A | 1/1999 | Chiba et al. |
| 5,931,811 A | 8/1999 | Haissaguerre et al. |
| 6,048,329 A | 4/2000 | Thompson et al. |

FOREIGN PATENT DOCUMENTS

| | | |
|---|---|---|
| JP | 4-42838 | 4/1992 |
| JP | 05-253175 | 10/1993 |
| JP | 06-292652 | 10/1994 |
| JP | 07-308884 | 11/1995 |
| JP | 07-328127 | 12/1995 |
| JP | 08-110480 | 4/1996 |
| JP | 11-48171 | 2/1999 |

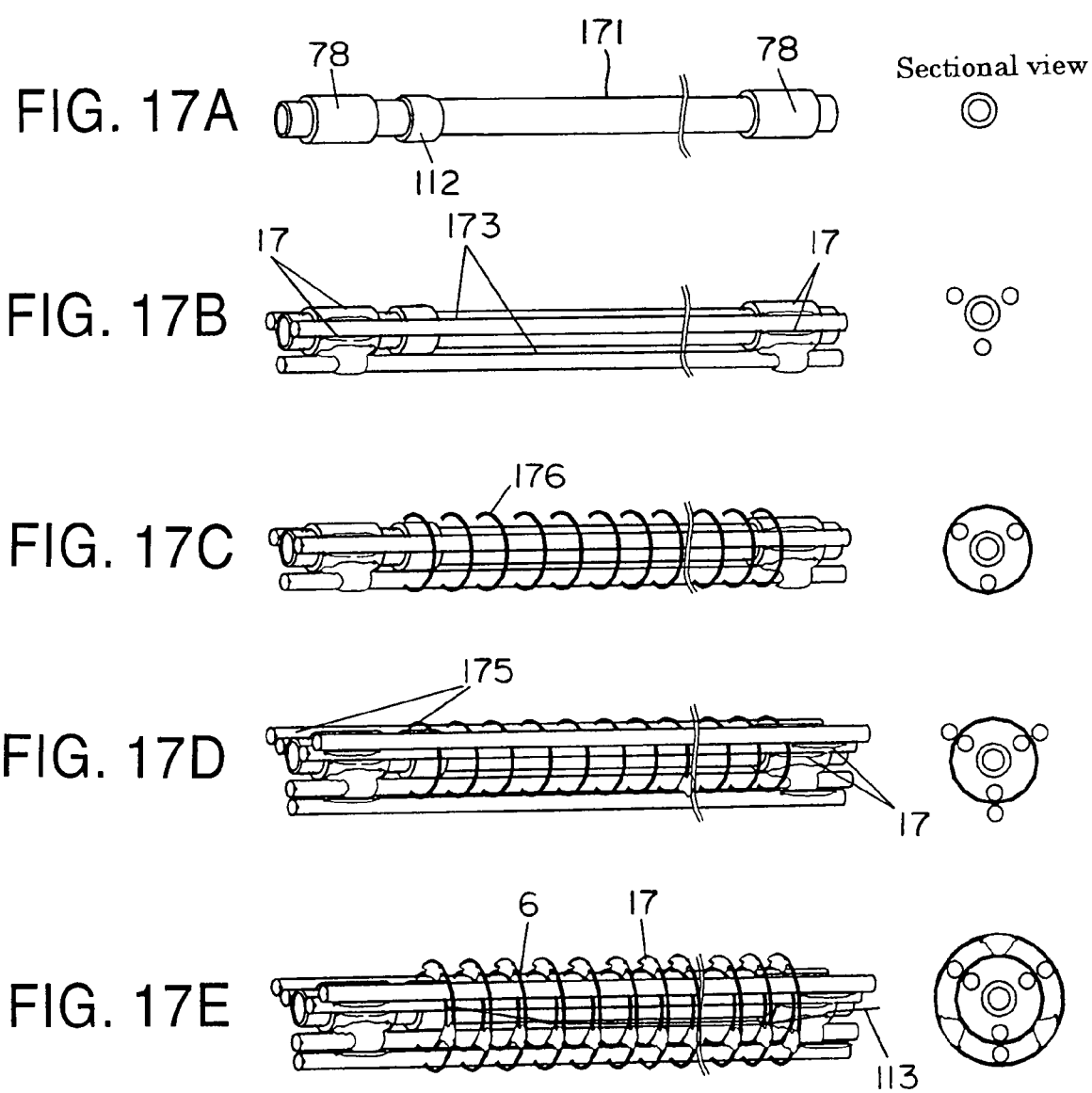

~~~NH⁺: acrylic resin of cation type dispersed in water [charged positively]

Ni⁺: Nickel Ion

~~~COO⁻, acrylic resin of anion type dispersed in water [charged negatively]

ACTIVE SLENDER TUBES AND METHOD OF MAKING THE SAME

RELATED APPLICATION

This application is a divisional of U.S. patent application Ser. No. 09/457,294 filed on Dec. 9, 1999, now U.S. Pat. No. 6,672,338 which is hereby incorporated by reference in its entirety. Priority under 35 U.S.C. §§120 and 121 is claimed for the benefit of the filing date of U.S. patent application Ser. No. 09/457,294.

TECHNICAL FIELD

The present invention relates in general to the field of micro electro mechanical systems (MEMS) for medical or non-medical use. More particularly, the invention relates to an active slender (small diameter) tube or tubular object or instrument that can be incorporated into a complex machine system or a pipe line to perform a machine inspection or system maintenance, or can be used as a medical micro electro mechanical systems such as an active catheter or an active guide wire as incorporated into a human blood vessel or organ for utilization in performing a diagnosis or medical treatment.

Such slender tubes or tubular objects as combined or assembled are also applicable to building an articulated or multi-articular, or multi-leg robot, or an elaborate toy.

BACKGROUND ART

In recent years there have been increasingly used endoscopes with driving wires for diagnosis of, e.g., the large intestine. And efforts have also been exerted in developing active catheters in which a shape memory alloy (hereinafter also referred to SMA) that is deformable when electrically heated is utilized to make up an actuator.

Further, with the progress of micro-machining technologies, efforts have been made to develop varieties of microsensors and active micromechanisms that may effectively be incorporated into catheters for medical applications.

For example, Japanese patent application No. H10-11258 filed Jan. 23, 1998 by the inventor of this application (JP Laid-Open publication No. H11-48171 published Feb. 23, 1999 proposes an active catheter of an outer skeleton type in which a liner coil is disposed outside of a plurality of, e.g., three, actuators which are made of a shape memory alloy. The SMA made actuators are electrically energized to permit the active catheter to be bent or flexed.

As to an extending and retracting mechanism for active catheters, there has been proposed an intra-tubular traveling apparatus having a tubular diameter of around 1 cm utilizing the inflation and contraction of a balloon under an atmospheric pressure, with which have been made on an experimental basis an endoscope guidance system for large intestines and a pipe orifice inspection guidance systems for town gas conduits (see "The World of Micro-mechanisms" by T. Hayashi et al, Journal of the Japan Society of Acoustics, Vol. 49, No. 8, 1993).

An extending and retracting mechanism having a number of balloons disposed on its side surfaces has also been proposed. This is designed to permit the catheter to be advanced in a blood vessel as the inflation of the balloons pushes them against the inner wall of the blood vessel and their contraction and expansion in its axial direction are repeated (see "Potential of microsystems in medicine", Minimally Invasive Therapy & Applied Technology, 4: 267–275, 1995, A. E. Guver et al).

Active slender tubes so far proposed, such as those catheters or the like described above have not yet been sufficient, however, in their bendability and extendibility achievable, nor have they been wide enough in their degrees of freedom of movement selectable. Furthermore, if a single catheter is sought to have many more functions, its limited diameter and the need for a sufficiently spacious working channel in it have restricted the number of wires that could be incorporated to an insufficient extent.

It should also be noted that in orienting a manually operated catheter or guide wire that is normally bent towards its distal end in the form of the letter "J" so as to allow it to enter, e.g., into one of two blood vessels at their junction, it has been common practice to attempt to rotate the catheter or guide wire at its proximal end or side in order to rotate it at that distal end. Then, if the catheter or guide wire has in its midway a loop or an intricate travel or span, the torque to act to transmit the rotation at the proximal end to the distal end may fail to be well transmitted through the body of the catheter or guide wire, resulting in an insufficient manner, thus an inaccurate rotation of the catheter or guide wire at the distal or its foremost end will occur. This may be called a poor torquability.

Further, when the catheter or guide wire is pushed at its proximal end in order to advance its distal end towards a target position in a blood vessel, if the catheter or guide wire has a loop or an intricate travel or span a deflection that would then occur in the body of the catheter or guide wire would tend to prevent the pushing force applied at the proximal end from being accurately transmitted to the distal end, thus resulting in an imprecise positioning of the catheter or guide wire at its foremost end. This may be called poor pushability.

On the other hand, positioning the catheter or guide wire by retraction can be achieved relatively accurately. However, this operation requires the catheter or guide wire to be first advanced beyond the target position. Stiffening the catheter or guide wire improves its pushability and torquability, but increases the risk of perforation. Conversely, if the stiffness is reduced too much, deflection would prevent the catheter or guide wire from advancing any further however hard it may be pushed.

SUMMARY OF THE INVENTION

With the foregoing disadvantages or inconveniences of the prior art borne in mind, it is accordingly an object of the present invention to provide an improved active slender (small diameter) tube or tubular object or instrument that can be embodied as an active catheter, guide wire or any other micro electro mechanical systems or a system's active micro-component as previously described.

It is also an object of the present invention to provide such a slender (small diameter) tube or tubular object or instrument that is simple in construction and has an expanded capability of movement, i.e., torsionally rotating, bending, extending and/or and retracting an active portion thereof, i.e., a portion thereof that is required to act, and/or adjusting stiffness of such a portion, to a required extent or extents with ease and precision.

It is also an object of the present invention to provide such a slender (small diameter) tube or tubular object or instrument of the outer skeleton type that meets the requirements described above.

Another object of the present invention is to provide an improved method of making such a slender (small diameter) tube or tubular object or instrument of the outer skeleton (exoskeletal) type that permits manufacture thereof with increased precision.

These and other objects which will become more readily apparent hereinafter are attained in accordance with the present invention.

According to the principles of the present invention in a first aspect thereof and in a certain form of implementation thereof, there is provided an active slender tube that is provided with a torsionally rotating mechanism. In specific terms, this form of implementation of the invention provides an active slender (small diameter) tube or tubular object or instrument that has a torsionally rotating mechanism mounted on or in the body portion thereof for torsionally rotating an active portion of the slender tube or tubular object or instrument as it is embodied, i.e., as an active catheter or guide wire or any other micro electro mechanical system or a system's active micro-component.

According to an alternative form of implementation of the principles of the present invention, there is provided an active slender tube that is provided with an extending and a retracting mechanism. In specific terms, the slender (small diameter) tube or tubular object or instrument has an extending and retracting mechanism mounted on or in the body portion thereof for extending and retracting an active portion of the slender tube or tubular object or instrument as it is embodied, i.e., as an active catheter or guide wire, or any other micro electro mechanical system or a system's active micro-component. The extending and retracting mechanism here comprises an elastically deformable outer skeleton that may include an outer elastically deformable tube or tubular member or element, and an extending and retracting actuator disposed inside the outer skeleton and secured or fastened thereto. The extending and retracting member is made of a shape memory alloy (SMA) and upon deformation to have a length varied from the length of the SMA made actuator in its natural shape memory state is secured or fastened to the elastically deformable outer skeleton.

According to a further alternative form of implementation of the principles of the present invention, there is provided an active slender tube that is provided with a stiffness control mechanism. In specific terms, this form of implementation of the principles of the present invention provides an active slender (small diameter) tube or tubular object or instrument that has a stiffness control mechanism mounted on or in the body portion thereof for controlling stiffness of an active portion, or the body portion, of the slender tube or tubular object or instrument towards its forward end thereof as it is embodied, i.e., as an active catheter or guide wire, or any other micro electro mechanical system or a system's active micro-component.

According to a specific form of implementation of the principles of the present invention, there is provided an active slender tube as described in any one of the preceding three paragraphs, that is further provided, specifically on or in the body portion of the active slender (small diameter) tube or tubular object or instrument, with a bending mechanism. The bending mechanism here is provided in particular adjacent to the active end portion of the slender tube or tubular object or instrument for bending the active end portion thereof as it is embodied, i.e., as an active catheter or guide wire or any other micro electro mechanical system or a system's active micro-component. The bending mechanism here comprises an elastically deformable outer skeleton that may include an outer elastically deformable tube or tubular member or element as above described, and has a bending actuator that is made of an SMA material.

According to a further alternative form of implementation of the principles of the present invention, there is provided an active slender (small diameter) tube or tubular object or instrument as embodied, e.g., as an active catheter or guide wire or any other micro electro mechanical system or a system's micro-component that comprises a bending mechanism, a torsionally rotating mechanism, an extending and retracting mechanism, and a stiffness control mechanism, which have an elastically deformable outer skeleton. Alternatively, it may comprise an elastically deformable outer skeleton, a bending mechanism, a torsionally rotating mechanism and a stiffness control mechanism. In specific terms, the elastically deformable outer skeleton may have a portion thereof that may be constituted by an outer elastically deformable tube or tubular member or element is common to all of the bending, torsionally rotating, extending and retracting, and stiffness control mechanisms, but should preferably have individual portions thereof that are in particular, specific to these separate mechanisms, respectively.

A further specific form of implementation of the principles of the present invention is characterized in that an elastically deformable outer skeleton or skeleton portion specifically provided for the bending mechanism as described above comprises a flat cable or wire type liner coil.

A further specific form of implementation of the principles of the present invention is characterized in that a torsionally rotating mechanism as described above comprises an elastically deformable outer skeleton and a torsionally rotating actuator disposed inside of the outer skeleton and secured thereto coaxially therewith. Here, the torsionally rotating actuator is made of a SMA material and upon deformation to have a diameter torsionally varied from the diameter of the SMA made actuator in its natural shape memory state is secured or fastened to the elastically deformable outer skeleton.

A further specific form of implementation of the principles of the present invention is characterized in that a stiffness control mechanism as described above comprises an elastically deformable outer skeleton and a stiffness control actuator disposed inside the elastically deformable outer skeleton and secured thereto coaxially therewith. Here, the stiffness control actuator is made of a SMA material and as in its natural shape memory state is secured or fastened to the elastically deformable outer skeleton.

A further specific form of implementation of the principles of the present invention is characterized in that each of a bending mechanism, a torsionally rotating mechanism, an extending and retracting mechanism and a stiffness control mechanism as described above, is provided at each of its opposite ends with electrode connectors.

A further specific form of implementation of the principles of the present invention is characterized in that an elastically deformable outer skeleton as described above, comprises a spiraled board having a plurality of wires incorporated therein with either of a spring structure of plastic made flat wires and a spring structure of insulator coated super-elastic alloy made flat wires.

A further specific form of implementation of the principles of the present invention is characterized in that a SMA made actuator member as described above has a flat cable or wire spring structure.

A further specific form of implementation of the principles of the present invention is characterized in that a flat cable or wire spring structure and SMA made actuator as described above has a heater provided therefor.

Such an active slender tube or tubular object or instrument as described above, when it is used as an active component of a micromachine system such as a catheter, guide wire or any other system's active micro-component as previously described, is found to be capable of readily bending, torsionally rotating, and/or extending and retracting, and/or adjusting stiffness of, its active portion to a required extent or extents with ease and precision.

An outer skeleton structure combined with a SMA made actuator as described above permits each to be configured in a flat spring structure and thus permits a greater number of thinner wires to be included in each of them.

Also, locating a SMA actuator member that is a heat emitting body inside an outer skeleton structure with enough distance from the surface of the active slender tube or tubular object or instrument can effectively limit the surface temperature up to or well below 41° C. that is tolerable for the human body.

In accordance with the principles of the present invention in a second aspect thereof and in another form of implementation thereof, there is also provided a method of making a slender (small diameter) tube or tubular object or instrument that maybe embodied, i.e, as an active catheter or guide wire or any other micromachine system or a system's active micro-component, which method comprises the steps of: preparing an actuator made of a shape memory alloy (SMA) and configured to form a portion of the slender tube or tubular object or instrument; disposing outside of the SMA made actuator and coaxially therewith an elastically deformable outer skeleton configured to form a portion of the slender tube or tubular object or instrument; and fastening the SMA made actuator member and the outer skeleton together.

A certain specific form of implementation of the principles of the present invention in the second aspect thereof is characterized in that the step of disposing described above includes a step of cladding a rod with the SMA made actuator member.

Another specific form of implementation of the principles of the present invention in the second aspect thereof is characterized in that the step of disposing described above includes steps of disposing a rod on the SMA made actuator member and cladding the rod with the outer skeleton.

Yet another specific form of implementation of the principles of the present invention in the second aspect thereof is characterized in that the step of disposing described above includes a step of cladding a pipe shaped jig that is triangular in cross section with the SMA made actuator member.

A further specific form of implementation of the principles of the present invention is characterized in that the step of disposing described above includes a step of electrically connecting a lead wire to the SMA made actuator member.

A further specific form of implementation of the principles of the present invention in the second aspect thereof is characterized in that the step of fastening described above includes a step of bonding the SMA made actuator member and the outer skeleton together with an adhesive.

An alternative specific form of implementation of the principles of the present invention in the second aspect thereof is characterized in that the step of disposing described above includes a step of forming non-insulated portions on the SMA made actuator member and the outer skeleton in their corresponding areas, and the step of fastening described above includes a step of passing an electric current through the SMA made actuator member and the outer skeleton in an electroplating liquid to deposit a metal on the non-insulated portions from the liquid and thereby to electrically join the actuator member and the outer skeleton together at those corresponding areas.

Another alternative specific form of implementation of the principles of the present invention in the second aspect thereof is characterized in that the step of disposing described above includes steps of forming non-insulated portions on the SMA made actuator member and the outer skeleton in their corresponding areas and disposing at least one lead wire adjacent to the non-insulated portions, and the step of fastening described above includes a step of passing an electric current through the lead wire, the SMA made actuator member and the outer skeleton in an electroplating bath to deposit a metal on the lead wire and the non-insulated portions from the liquid and thereby to electrically join the actuator member, the outer skeleton and the lead wire together in those corresponding areas.

Another alternative specific form of implementation of the principles of the present invention in the second aspect thereof is characterized in that the step of disposing described above includes a step of forming non-insulated portions on the SMA made actuator member and the outer skeleton in their corresponding areas, and the step of fastening described above includes a step of passing an electric current through the SMA made actuator member and the outer skeleton in a liquid containing an insulating resin to electro-deposit the insulating resin on the said non-insulated portions from the liquid and thereby to join the actuator member and the outer skeleton together at those corresponding areas.

Another alternative specific form of implementation of the principles of the present invention in the second aspect thereof is characterized in that the step of disposing described above, includes steps of forming a non-insulated portion on the SMA made actuator member and electroplating the non-insulated portion to form an electrically conductive junction thereat, and the step of fastening described above includes a step of passing an electric current through the SMA made actuator member and the outer skeleton in a liquid containing an insulating resin to electro-deposit the insulating resin on the non-insulated portion and throughout, on the outer skeleton from the liquid solution and thereby to join the actuator member and the outer skeleton together.

A further specific form of implementation of the principles of the present invention in the second aspect thereof is characterized by further steps of forming non-insulated portions on the SMA made actuator member and the outer skeleton and passing an electric current through the SMA made actuator member and the outer skeleton in an electroplating bath to deposit a metal on the non-insulated portions from the bath and thereby to electrically join the actuator member and the outer skeleton together.

A further specific form of implementation of the principles of the present invention in the second aspect thereof is characterized by a further step of removing natural oxide layer on the SMA made actuator member and the outer skeleton immediately prior to depositing the metal and/or insulating resin, respectively.

A further specific form of implementation of the principles of the present invention in the second aspect thereof is characterized by a further step of drying by vacuum drying.

A further specific form of implementation of the principles of the present invention in the second aspect thereof is characterized in that, in the step of disposing described above, the SMA made actuator member is disposed so as to be elastically deformable.

The method as described above of making a slender (small diameter) tube or tubular object or instrument is found to permit manufacture of such slender tubes or tubular objects or instruments with increased precision.

Also, if fastening is carried out by electric metal plating or resin deposition, it can be effected at a number of points of connection simultaneously.

These and other features, objects and advantages will be understood and become more readily apparent to those of ordinary skill in the art, from the following detailed description of the preferred embodiments as illustrated in the various drawing figures in the accompanying drawings.

BRIEF DESCRIPTION OF THE DRAWINGS

In the accompanying drawings:

FIGS. 17A, 17B, 17C, 17D and 17E are views that together show a flow chart that indicates how a guide wire of an outer skeleton type can be assembled in one way according to another form of the present invention;

BEST MODES FOR CARRYING OUT THE INVENTION

Figure 1:
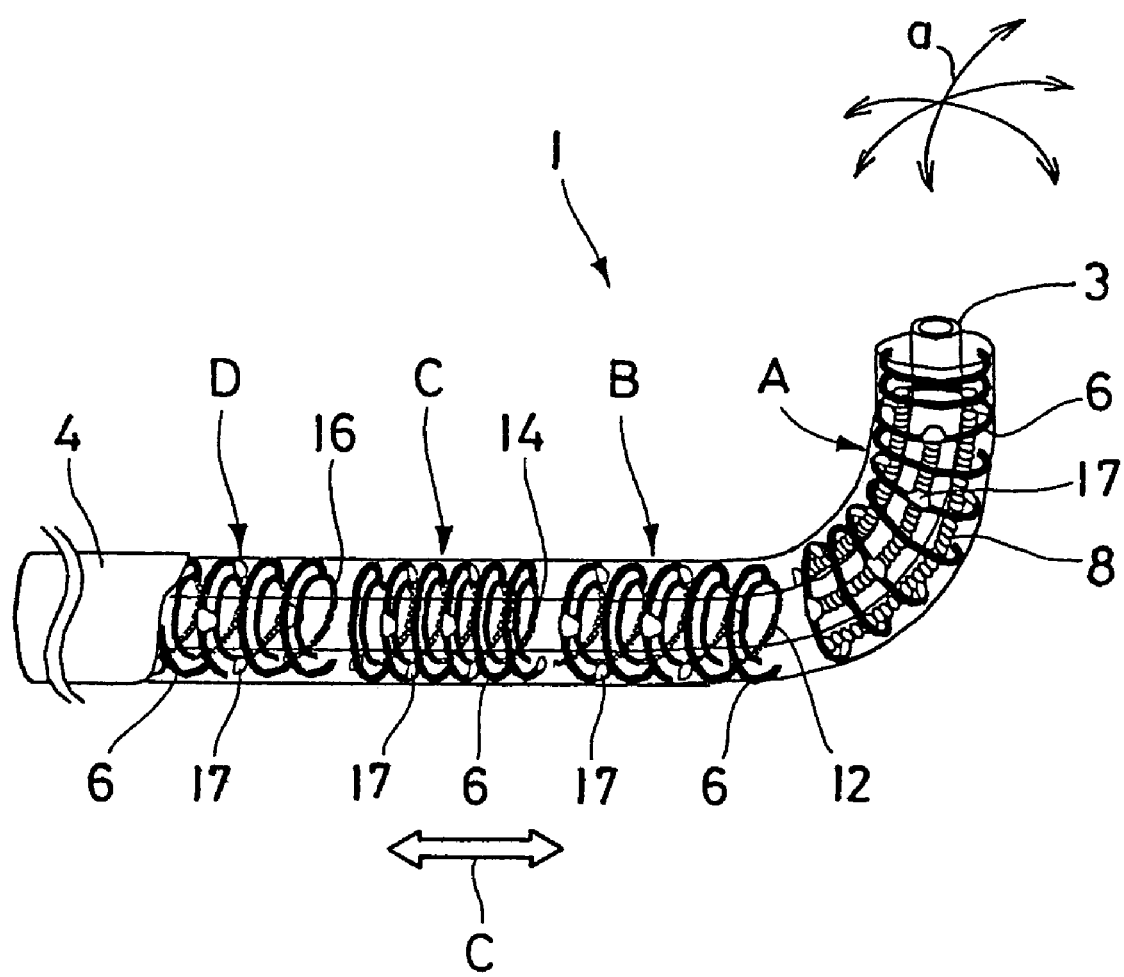
FIG. 1 is a view in part perspective of an active catheter that represents a first form of embodiment of the present invention.

Hereinafter, suitable embodiments as preferred of the present invention with respect to an improved active slender (small diameter) tube or tubular object or instrument (here-after simply referred to as "slender tube") that can be embodied as a medical or non-medical micromachine system or system's active micro-component, and a method of making the same, are set out with reference to the various figures in the accompanying drawings hereof An active slender tube embodied as an active catheter according to a certain form of embodiment of the present invention is depicted in FIG. 1 in part perspective view thereof.

In FIG. 1, an active catheter 1 according to this form of embodiment is shown to include four portions, in an active, distal end portion of the catheter where it is seen curved in the form of the letter "J", where a bending or flexing mechanism A, a torsionally rotating mechanism B, an extending and retracting mechanism C and a stiffness control mechanism D are provided, respectively. The bending mechanism A is provided in the most distal portion of the "J". The torsionally rotating mechanism B is provided in a region of the root of J-shaped curvature and connected to the bending mechanism A. The extending and retracting mechanism C is provided in a linear portion of J-shaped curvature and connected to the torsionally rotating mechanism B. The stiffness control mechanism D is provided in a proximal side of the J-shaped curvature and connected to the extending and retracting mechanism C. These independent mechanisms A, B, C and D lie in an annular space defined by both an inner flexible tube 3 having a working channel therein and a thin, flexible outer tube 4 composed of, e.g. silicone rubber that may have a single, continuous liner coil 6 associated therewith as shown in FIG. 1.

The bending mechanism A includes a liner coil 6 arranged to back the surface of the inner wall of the outer tube 4. Disposed inside the liner coil 6 that forms an outer skeleton (exoskeleton) together with the outer tube 4, a bending actuator member 8 comprises one or more (three as shown) densely wound spring coils made up of a shape memory alloy (SMA) which or each of which individually, is fastened to the liner coil 6, preferably at a plurality of points, by means of an electrically conductive adhesive 17, forming bending actuator elements. When so fastened to the liner coil 6, each of the three SMA made actuator coils 8 shown has a number of joints. When a coil segment constituting each bending actuator element with a given length between adjacent joints is heated with an electric current passed therethrough, the coil segment or element will shrink and bend the active distal end of the catheter. While provision of a number of joints is preferred to make the active distal end of the catheter 1 articulated, even a single joint is still operative. In this embodiment, the three SMA made bending actuator coils 8 are provided to make the active distal end portion of the catheter bendable in three independent directions. The liner coil 6 has an insulating coating while the actuator coils 8 are used freely of such coating. This applies to those in the other moving mechanisms B, C and D as well.

The torsionally rotating mechanism B includes a liner coil 6 arranged to back the surface of the inner wall of the outer tube 4. Disposed inside of the liner coil 6 and coaxially therewith, a torsionally rotating actuator member 12 comprises a coil in the form of a spring with a space between adjacent turns, and made up of a SMA and fastened to the liner coil 6 at its suitable sites by means of an electrically nonconductive adhesive 17. The SMA made torsionally rotating actuator coil 12 should, upon deformation to have a diameter somewhat larger than a diameter thereof in its natural shape memory state, be fastened to the liner coil 6 that together with the outer tube 4 forms an outer skeleton (exoskeleton) for the SMA made torsionally rotating actuator member 12. In the embodiment shown, the SMA made torsionally rotating actuator coil 12 is arranged to have a single joint or coil segment that is heated with an electric current passed therethrough to shrink, thereby torsionally rotating the active distal end portion of the catheter 1. Of course, the coil 12 may be provided with a plurality of such joints or coil segments with a given length as actuator elements, to be heated with electric current separately.

The extending and retracting mechanism C includes a liner coil 6 arranged to back a surface of the inner wall of the outer tube 4. Disposed inside the liner coil 6 and coaxially therewith, an extending and retracting actuator member 14 comprises a coil in the form of a spring with a space between adjacent turns, and made up of a SMA and fastened to the liner coil 6 at its suitable sites by means of an electrically nonconductive adhesive 17. The SMA made extending and retracting actuator coil 14 before being so fastened is deformed to somewhat compress and is prepared to have, when so fastened, the same length as the liner coil 6 that together with the outer tube 4 forms an outer skeleton (exoskeleton) for the SMA made extending and retracting actuator member 14. In the embodiment shown, the SMA made extending and retracting actuator coil 14 is arranged to have a single joint or coil segment that is heated with an electric current passed therethrough to extend in order to restore its natural length, thereby extending the active distal end portion of the catheter 1. When the electric current is cut off, the actuator coil 14 is allowed to shrink, thereby retracting the catheter's active distal end portion. Of course, the coil 12 may be provided with a plurality of such joints or coil segments with a given length as actuator elements to be heated with an electric current separately.

The stiffness control mechanism D includes a liner coil 6 arranged to back the surface of the inner wall of the outer tube 4. Disposed inside of the liner coil 6 and coaxially therewith, a stiffness control actuator member 16 comprises a coil in the form of a spring with a space between adjacent turns, and made up of a SMA and fastened to the liner coil 6 at its designated sites by means of an electrically nonconductive adhesive 17. The SMA made stiffness control actuator coil 16 is fastened with a length in its natural state to the liner coil 6 that together with the outer tube 4 an outer skeleton (exoskeleton) for the stiffness control actuator member 16. In the embodiment shown, the SMA made stiffness control actuator coil 16 is arranged to have a single joint or coil segment that is heated with an electric current passed therethrough to stiffen itself, thereby stiffening, without deforming, the J-shaped active distal end portion of the catheter 1. When the heating electric current is cut off, the actuator coil 16 is allowed to soften itself, thereby softening, without deforming, the catheter's J-shaped active distal end portion. Of course, the coil 16 may be provided with a plurality of such joints or coil segments with a given length as actuator elements to be heated with an electric current separately.

The liner coil 6 is designed to be elastically deformable, together with the outer and inner flexible tubes 3 and 4, when each of the SMA actuator coils 8, 12 and 14 is heated with an electric current passed therethrough and cooled with the current cut off. The mechanisms A, B, C and D may each have a portion or portions fastened to the inner tube 3 as well, and also need not necessarily be interconnected as shown and may have their interconnection modified in any suitable order.

The construction as shown and described above in which each of the liner coils 6 and each corresponding actuator coil 8, 12, 14, 16 are confined in an annular space defined by the inner and outer flexible tubes 3 and 4 make them form a tube or tubular object or instrument and constitute geometrical components thereof.

A slender tube embodied as an active catheter 1 according to the first form of embodiment with the construction as shown in FIG. 1 and described above is capable of moving the J-shaped active distal end of the catheter as required, e.g., bending it in three independent directions as shown by the arrows a, torsionally rotating it as shown by the arrow b and extending and retracting (moving forth and back) it as shown by the arrow c, and is capable of holding it in an adequately stiffened or softened state, by applying an electrical heating current to a part forming a joint in each of the mechanisms.

A fluid can be injected into, or drawn out of, an opening provided at the distal end of the inner tube 3 of the catheter 1. Alternatively, a micro-tool guided through the working channel in the inner tube 3 may be allowed to go out and come into it through that opening.

A slender tube embodied as shown and described, can thus be applied to a diagnosis and a treatment in medicine, and can also be used as any tubular instrument for testing or inspection and maintenance of a is complex machine or piping system.

Figure 2:
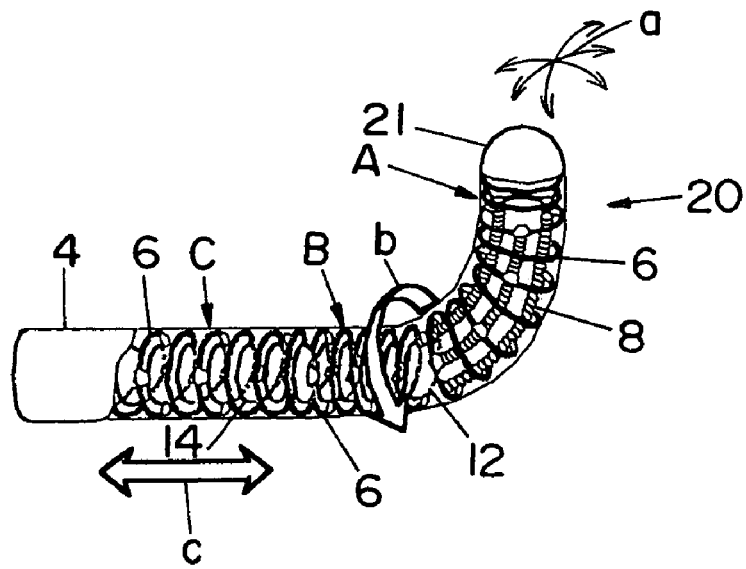
FIG. 2 is a view in part perspective of an active guide wire that represents a second form of embodiment of the present invention, the guide wire being here bendable in three directions.

FIG. 2 shows, in part perspective, an active guide wire bendable in three directions, that represents a second form of embodiment of the present invention. A slender tube embodied as an active guide wire 20 in this form of embodiment is devoid of the inner tube 3 provided in the catheter according to the first form of embodiment, but is still hollow to retain a tubular configuration that is further reduced in its outer and inner diameters. The guide wire 20 is provided at its distal end, i.e., the foremost end of the J-shaped active distal end portion, with a cap 21 that is shaped in the form of a semi-sphere to seal the hollow interior of the guide wire 20 as so embodied and to provided an adequate touching end of guide wires. A stiffness control mechanism is not shown in FIG. 2, but may be provided as connected to an extending and retracting mechanism in this form of embodiment as in FIG. 1.

Each liner coil 6 is here again adapted to be elastically deformable, together with the outer flexible tube 4, when a SMA made actuator 8, 12, 14 is heated with an electric current passed therethrough and to be returned to its original state when the current is cut off. The mechanisms may be arranged separately and independently of others, or they may alternatively be interconnected with a link or links.

Movements achieved for the J-shaped active end portion by the second form of embodiment are essentially the same as those previously described for the first form of embodiment.

Figure 3:
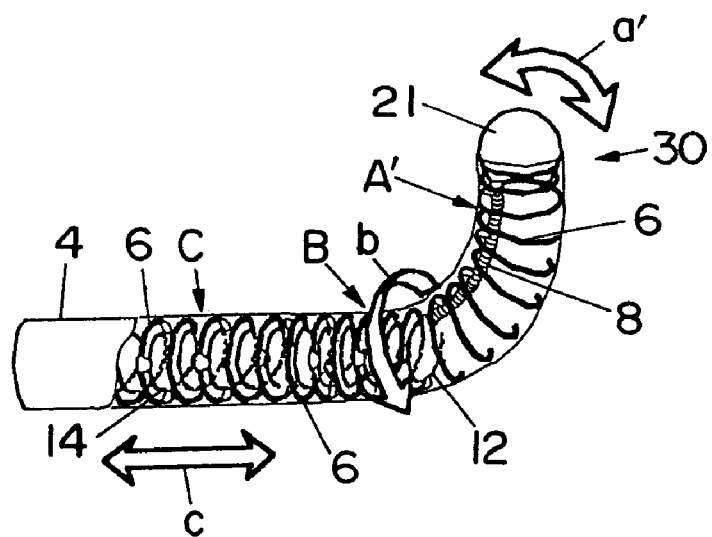
FIG. 3 is a view in part perspective of an active guide wire that represents a third form of embodiment of the present invention, the guide wire being here, bendable in one direction.

FIG. 3 shows, in part perspective, an active guide wire bendable in one direction, which represents a third form of embodiment of the present invention.

In the guide wire 30 shown in FIG. 3 according to the third form of embodiment, a bending mechanism A' has only one SMA made actuator member coil 8 and allows a bending motion for the J-shaped active distal is end portion of the guide wire in one direction as shown by the arrow a'. The other movements achieved by this form of embodiment are the same as in the second form of embodiment shown in FIG. 2. While a stiffness control mechanism D is not shown in FIG. 3, it may be provided as connected to the extending and retracting mechanism C in this form of embodiment as well as shown in FIG. 1.

Figure 4:
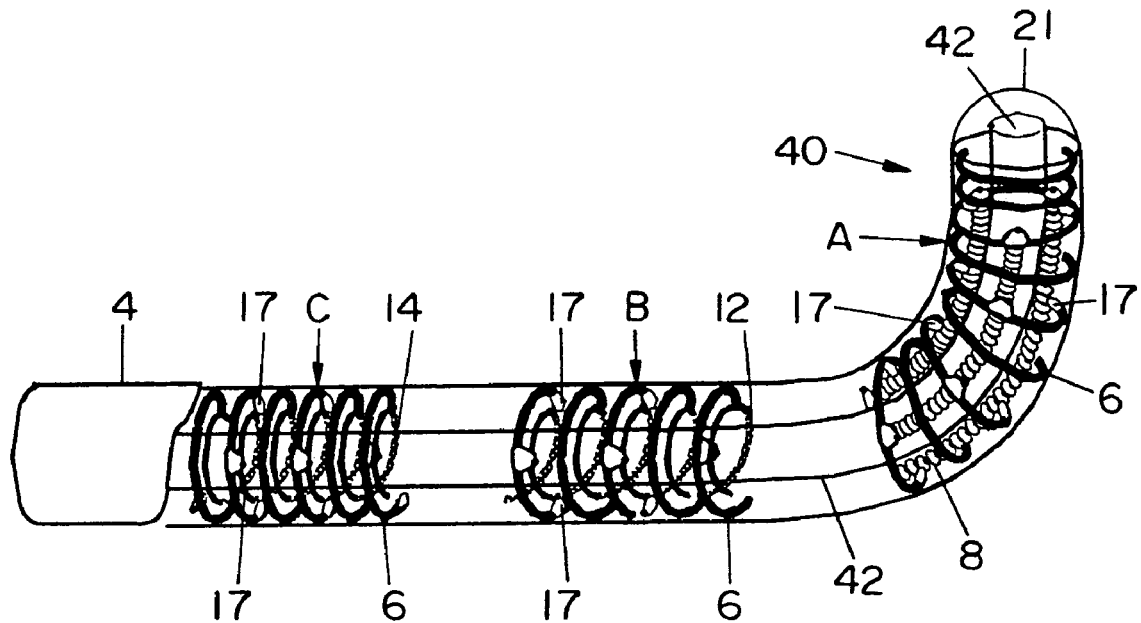
FIG. 4 is a view in part perspective of an active guide wire having a splicing wire element which represents a fourth form of embodiment of the present invention.

FIG. 4 shows, in part perspective, an active guide wire having a connecting wire, that is according to a fourth form of embodiment of the present invention. While in FIG. 4 a stiffness control mechanism D is not shown, it may be provided as connected to the extending and retracting mechanism C in this form of embodiment as well as shown in FIG. 1.

As shown in FIG. 4, the active guide wire 40 according to the fourth form of embodiment replaces the inner tube 3 in the active catheter according to the first form of embodiment with a flexible connecting wire 42 that passes through the hollow or tubular configuration to ensure centering each for the bending mechanism A, the torsional rotating mechanism B, the extending and retracting mechanism C and further the stiffness control mechanism D. The guide wire 40, here too, is further reduced in its diameter. The movements achieved for the active distal end portion by the fourth form of embodiment are essentially the same as by the first form of embodiment.

Figure 5:
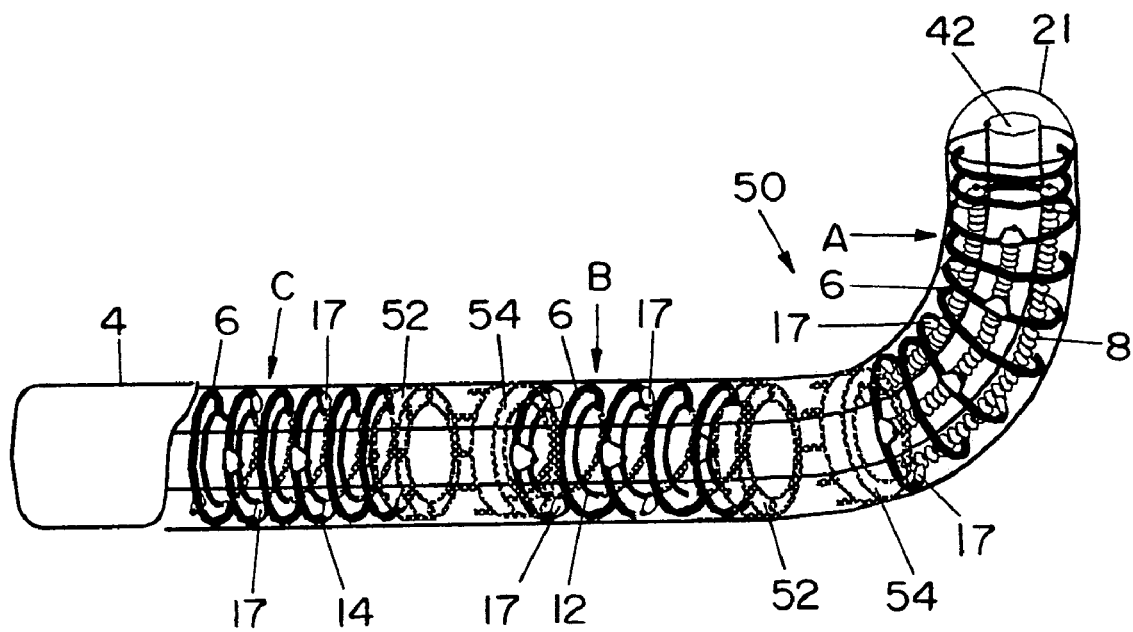
FIG. 5 is a view in part perspective of an active guide wire that represents a fifth form of embodiment of the present invention.

FIG. 5 shows, in part perspective, an active guide wire according to a fifth form of embodiment of the present invention. While in FIG. 5 a stiffness control mechanism D is not shown, it may be provided as connected to the extending and retracting mechanism C in this form of embodiment as well as shown in FIG. 1.

Figure 6:
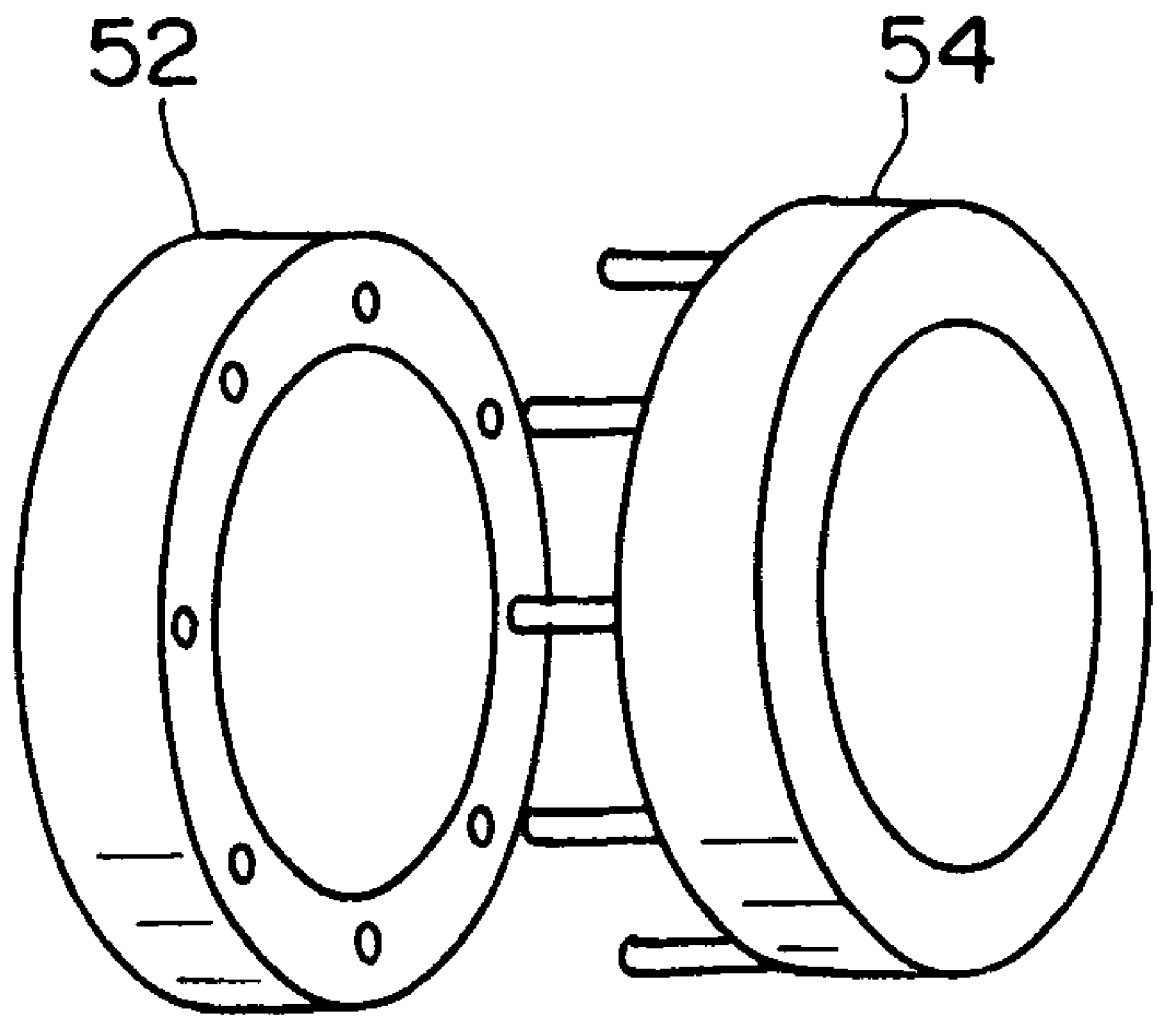
FIG. 6 is a view of appearance of a male and a female electrode connector that represents the fifth form of embodiment of the present invention.

Referring to FIGS. 5 and 6, a guide wire 50 according to the fifth form of embodiment has two adjacent actuator mechanisms in the guide wire 40 according to the fourth form of embodiment interconnected with a male electrode connector 54 and a female electrode connector 52. Specifically, as shown, the bending mechanism A is provided at its proximal end with a male or female electrode connector 54, 52 connected to a female or male electrode connector 52, 54 provided at the distal end of the torsionally rotating actuator mechanism B which is in turn provided at its proximal end with a male or female electrode connector 54, 52 connected to a female or male electrode connector 52, 54 provided at the distal end of the extending and retracting actuator mechanism C. The actuator mechanisms A, B, C and D are thus made mutually electrically conductive.

This arrangement permits the bending mechanism A, the torsionally rotating mechanism B, the extending and retracting mechanism C and the stiffness control mechanism D to be fabricated each as an independent module that can easily be assembled with and disassembled from those for the others.

The connecting wire 42 in the fifth form of embodiment can be replaced with an inner tube 3 shown in FIG. 1 to provide an active catheter having a working channel and a ring structure with a male and a female electrode connector 54, 52.

A description will now be made in detail of each of the mechanisms A, B, C and D.

Figure 7:
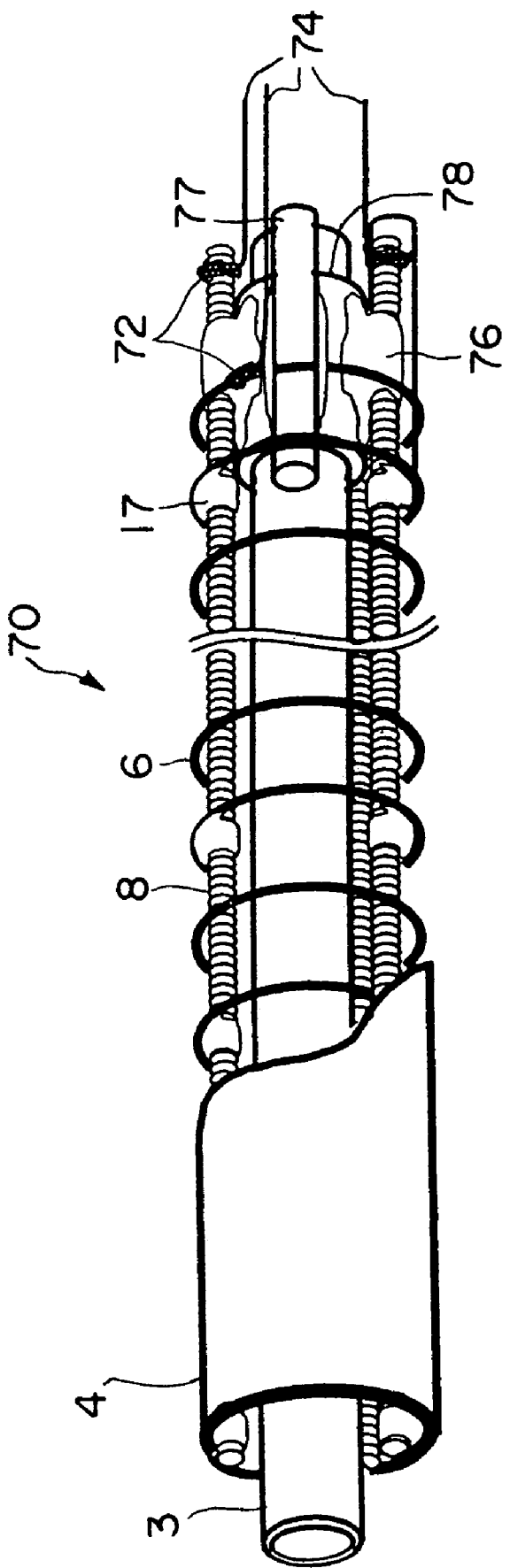
FIG. 7 is a view in part perspective of a bending movement mechanism of an active catheter according to the present invention.

FIG. 7 shows, in part perspective, a bending mechanism 70 for an active catheter.

Referring to FIG. 7, the bending actuator mechanism 70 includes a liner coil 6 arranged to back a surface of the inner wall of an outer tube 4 and coated with an insulating material. Disposed inside the liner coil 6 coaxially therewith, a SMA made bending actuator member 8 is provided in the form of one or more (three as shown) densely wound spring coils each of which is secured to the liner coil 6 in electrical contact therewith by means of a conductive adhesive 72. Each of the bending actuator coils 8 is also secured at its suitable sites to the liner coil 6 with an electrically nonconductive adhesive 17. An inner tube 3 is arranged to extend along the longitudinal axis of the active catheter.

So constructed and arranged, each of the SMA made bending actuator coils 8 has a multi-jointed structure and has a plurality of joint segments or parts, each of which can be heated with an electric current applied therethrough from a power supply via a lead wire. Three such lead wires 74 are fastened to the SMA actuator coils 8 and one to the liner coil 6 with a conductive adhesive 72 to establish the required electrical connections. A metal rod 77 and a holder 78 fastened to the SMA actuator coils 8 with a nonconductive adhesive 76 are used to assemble the mechanism and may be left to form a link therefor. If the inner tube 3 is eliminated or replaced by a connecting wire 42 as previously described, they may serve as an additional component for the guide wire bending actuator mechanism.

Figure 8:
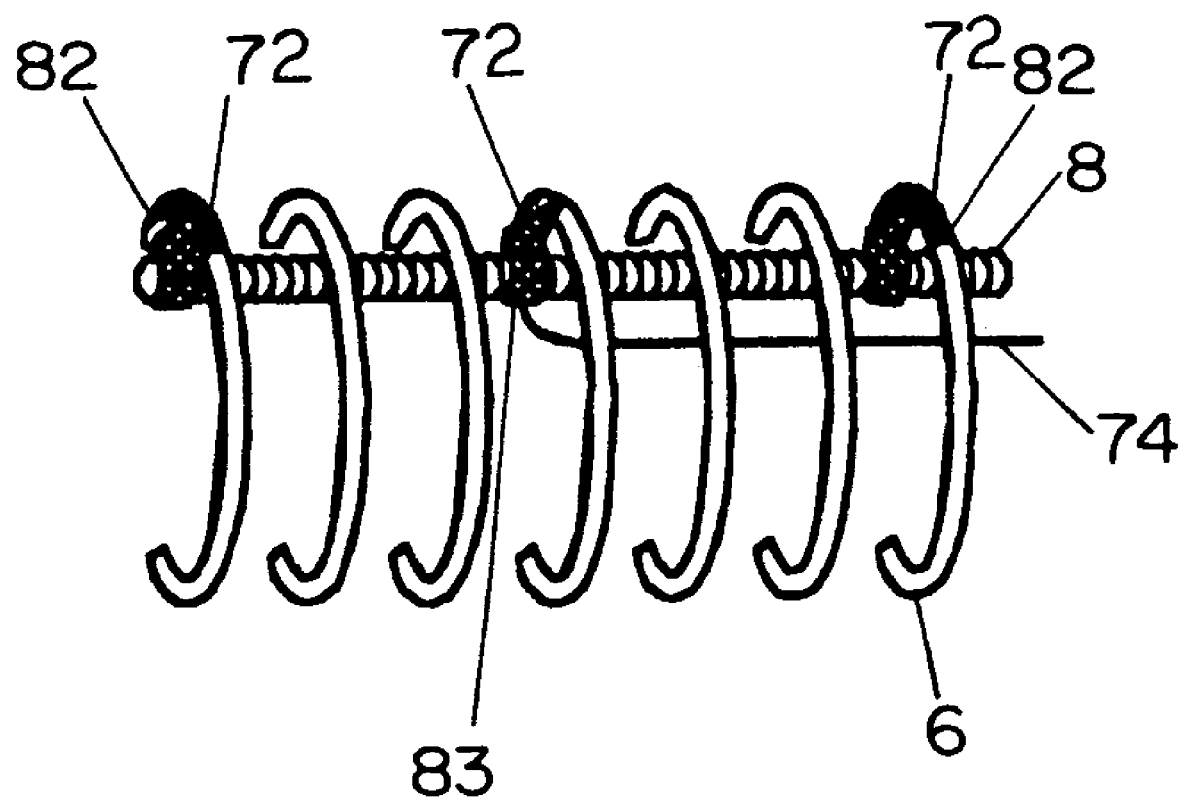
FIG. 8 is a detailed view that depicts how a lead wire is connected.
Figure 9A:
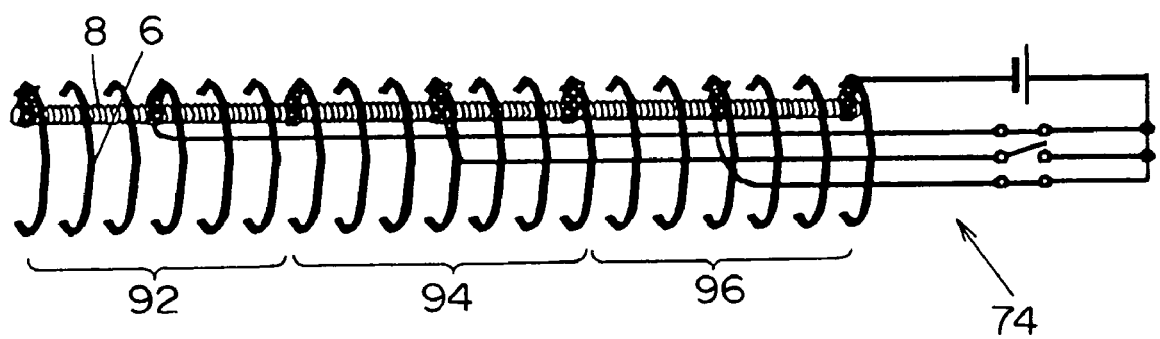
FIG. 9A is a view that shows an actual circuit (a)
Figure 9B:
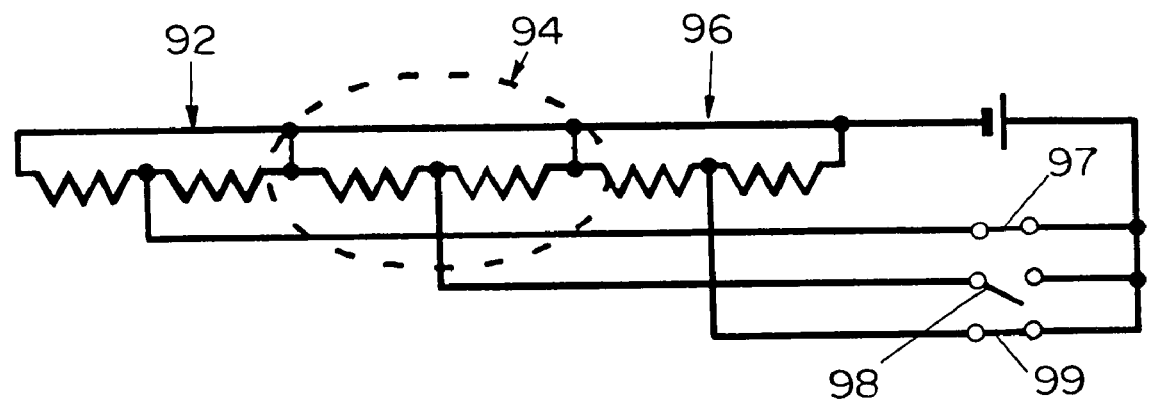
FIG. 9B is a view that shows an equivalent circuit (b)

FIG. 8 shows in detail, where and how a SMA actuator coil 8 is fastened to the liner coil 6 and a lead wire 74 is connected to the SMA actuator coil. FIG. 9A shows an actual circuit (a) and FIG. 9B shows an equivalent circuit thereof. In these Figures, a single SMA actuator coil 8 alone is shown for the sake of simplicity.

As shown in FIG. 8, the insulating coating is removed from the liner coil 6 locally at a site 82 and the liner coil 6 is then bonded there to the SMA actuator coil 8 with a conductive adhesive 72 to establish an electrical connection with the SMA actuator coil 8. At a site 83 on the liner coil 6 where the insulating coating remains unremoved and the liner coil 6 is fastened to the SMA actuator coil 8, the lead wire 74 is fastened to and electrically connected to the SMA actuator coil 8 to establish an electrical connection therewith. The liner coil 6 is grounded.

FIG. 9A shows a exemplary multi-joint SMA actuator coil 8 arrangement in which the SMA actuator coil 8 is divided into three coil parts or segments 92, 94 and 96 each of which is designed to form an articulation or "joint" and is defined between two adjacent sites 82 where the SMA actuator coil 8 is fastened mechanically to, and also connected electrically with, the liner coil. Lead wires 74 are fastened to and electrically connected to the actuator coil 8 at those sites 83, which represent the centers of coil segments 92, 94 and 96, respectively, and where the SMA actuator coil 8 is fastened in electrical isolation to the liner coil 6. These SMA actuator coil segments 92, 94 and 96 form resistors in an electrical circuit, and the liner coil 6 has a resistance negligible compared with the total resistance of the actuator coil 8 and even with the resistance of each of the actuator coil segments 92, 94 and 96. Thus, for passing electric heating current through these coil segments 92, 94 and/or 96 selectively, three parallel circuits that are formed across one terminal of the liner coil 6 on the one hand and the above mentioned three leads 74 on the other hand, respectively, has an equivalent circuit as shown in FIG. 9B. with respective on/off switches 97, 98 and 99 provided. Since the current is divided to flow according to resistance, if, for example, only the first and third switches 97 and 99 are turned on while leaving off the second switch 98 to pass an electric current selectively through the first and third coil segments 92 and 96 and thereby to selectively heat them, current flowing through the second actuator 94 is negligibly low with the result that only the first and third SMA actuator coil segments 92 and 96 are heated and thereby deformed (in this case, shrink).

If male and female electrode connectors (52, 54) as shown in FIGS. 5 and 6 are used, the liner coil 6 that is grounded should be formed to have one common terminal for an electrical circuit formed with the other terminals provided and connected corresponding to the actuator coil segments 92, 94 and 96, respectively.

SMA actuator coils 8 can be prepared with each having an outer diameter, e.g, of 250 micrometers with a coil wire diameter of 50 micrometers. A liner coil 6 made of, e.g., stainless steel may have an insulating coating, e.g., of a thermosetting acrylic resin electro-deposited thereon and may have an outer diameter of 1.1 to 1.3 mm and a coil wire diameter of 100 micrometers. If the coil wire needs to be reduced further in diameter, it can be etched with nitrohydrochloric acid to produce a wire with an outer diameter of 80 micrometers, further thinned.

A holder member for fastening a liner coil and a SMA actuator coil or coils may make use of, e.g., a polyimide tube with a diameter of 0.4 to 0.5 mm. An assembling metal rod may have a diameter of 0.3 mm, and a conductive adhesive may make use of an epoxy resin with a silver filler.

Prepared from such members, an assembly may be fitted in, an outer tube of an outer diameter of 1.3 mm, to form an active tubular guide wire of linkless and outer skeleton type without an inner tube, provided with a multi-joint, multi-degree-of-freedom moving mechanism having an outer diameter of 1.4 mm.

Figure 10:
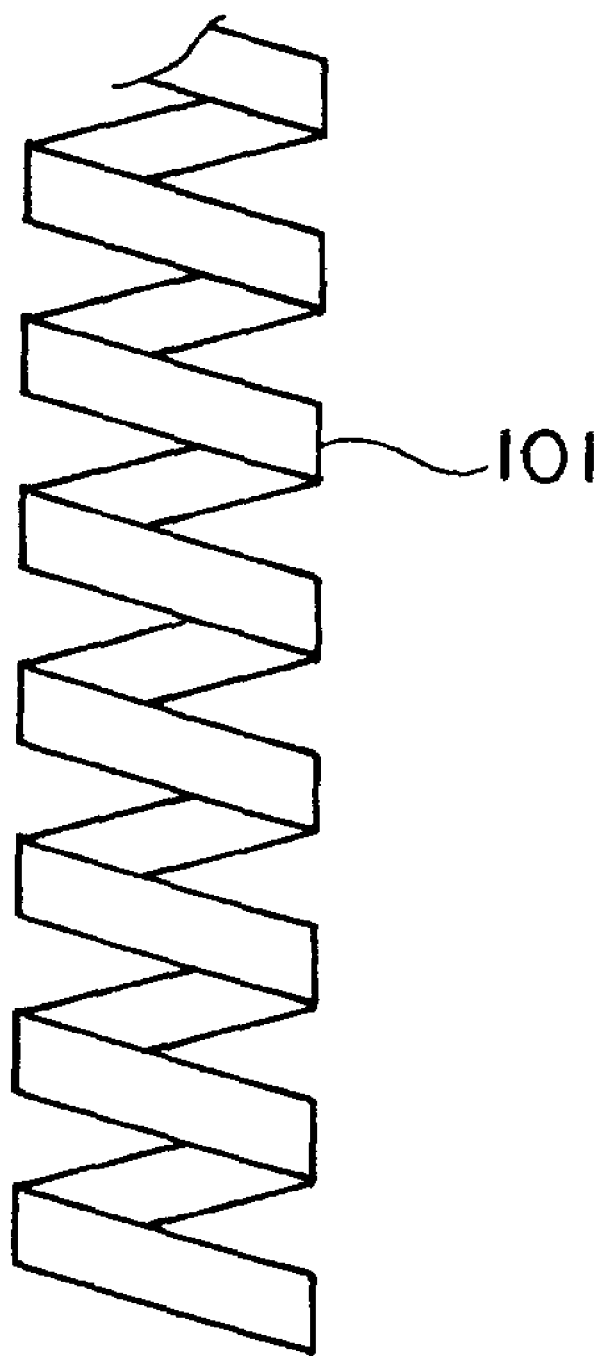
FIG. 10 is a plane view that shows a flat wire type liner coil.

FIG. 10 shows a flat wire liner coil 101 that can be employed to the advantage that it has an increased stiffness in its longitudinal direction while possessing an adequate stiffness in its transverse directions, hence to provide excellent bendability or lateral deformability to bend an active portion as used in the bending actuator mechanism.

As used in a mono- or multi-directional type bending actuator mechanism as previously described, a liner coil 101 so configured bends to provide for its active portion, bending and restoring movements, with an enhanced quality in each of a number of the directions given depending on the number of SMA bending actuators provided, when the liner coil 101 is laterally deformed from and restored to its original position with shrinkage and expansion of a given SMA actuator coil joint portion produced by its electrical heating or cooling.

An explanation will next be given in more detail of the torsionally rotating mechanism previously described.

Figure 11A:
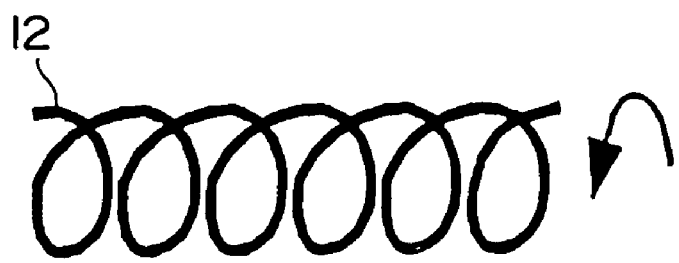
FIG. 11A is a view that illustrates a SMA actuator in its memory state for a torsionally rotating mechanism.
Figure 11B:
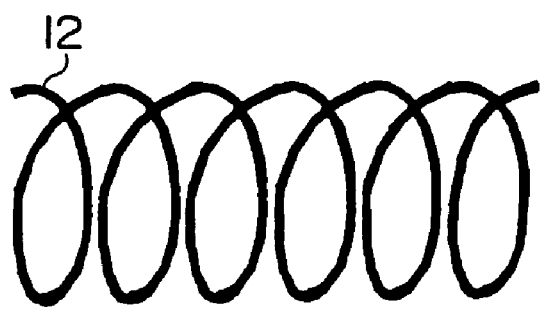
FIG. 11B is a view that illustrates the SMA actuator of the torsionally rotating mechanism that on a torsional rotation is enlarged in diameter from its shape memory state.
Figure 11C:
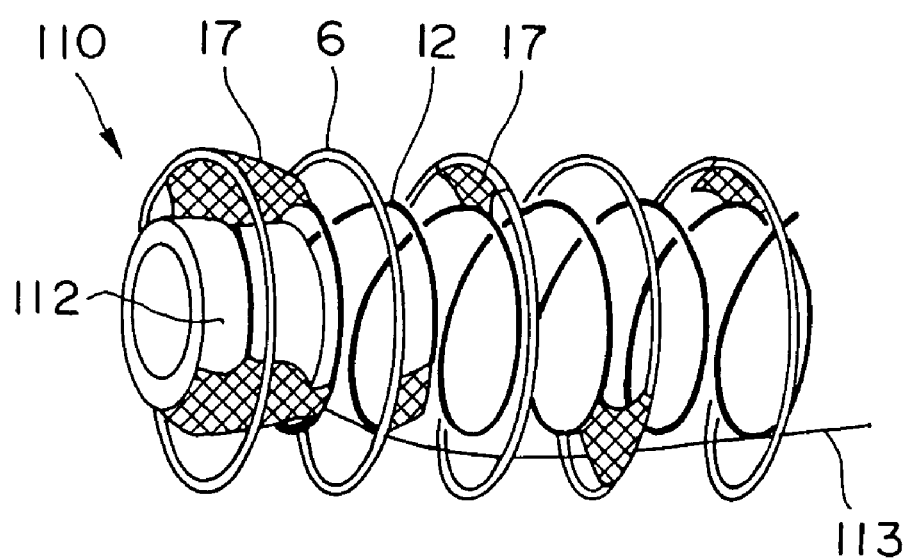
FIG. 11C is an appearance view of the torsionally rotating actuator mechanism.

FIGS. 11A, 11B and 11C are views showing essences of the torsionally rotating actuator mechanism, with FIG. 11A depicting the SMA made torsionally rotating actuator coil 12 in its natural shaped memory state. FIG. 11B depicts the SMA actuator coil 12 that is torsionally rotated to have resultingly a diameter somewhat increased from the diameter of itself in its natural memory state. FIG. 11C is an appearance view of a torsionally rotating mechanism 110.

The torsionally rotating mechanism 110 as shown in FIG. 11C is designed for an active guide wire, and is shown to omit, for the sake of simplicity, certain elements previously described such as the outer tube 4 (FIGS. 2–5) and the connecting wire 42 (FIGS. 4 and 5), and the cap 21 (FIGS. 2–5) that can be used to fit a polymer made fixing tube 112 shown. If the fixing tube 112 is replaced with an inner tube 3 shown in FIG. 1, there results an active catheter with its diameter variable. Description will be given below with primary reference with active guide wires.

Referring to FIGS. 11A, 11B and 1C, the torsionally rotating mechanism 110 makes use of an SMA made coil actuator 12 which is disposed inside a liner coil 6 and fastened thereto coaxially therewith as previously described. Here, the SMA coil actuator 12 when so fastened, has been deformed as torsionally rotated to have a coil diameter somewhat enlarged from its shape memory state, i.e., its original, natural or undeformed state. A nonconductive adhesive 17 is used to fasten the SMA torsionally rotating coil actuator 12 to the liner coil 6 at selected sites. The opposite ends of the SMA coil actuator 12 are fastened to those of the liner coil 6 on the fixing tubes 112 and 112 with a nonconductive adhesive 17.

Further, lead wires 113 are connected to the opposite ends of the SMA coil actuator 12 to permit it to be heated with an electric current passed therethrough.

If the liner coil 6 is grounded at one end commonly for its entirety, the SMA coil actuator 12 and the liner coil 6 may be electrically connected with each other via the fixing tube 112, and the SMA coil actuator 12 at its opposite end may be connected to a lead wire to permit it to be heated with an electric current passed therethrough.

The angle of torsional rotation effected by the mechanism 110 is related to the pitches of the SMA coil actuator 12 and the liner coil 6 as well as the ratio of these pitches and the ratio the wire diameters of the SMA coil actuator 12 and the liner coil 6. Thus, the higher the SMA coil actuator 12 in such ratios, the greater the maximum angle of torsional rotation obtained. An optimum setting for the angle of torsional rotation is made possible by the adjustment of those ratios.

The fixing tube 112 may be provided at each of the distal and proximal ends of the mechanism 110 and may be a polyurethane made tube having an outer diameter of 0.89 to 1.47 mm. The SMA coil actuator 12 may have a coil outer diameter of 1.6 to 1.8 mm with a pitch of 0.8 mm and a wire diameter of 100 micrometers. The liner coil 6 may be made of stainless steel and have a diameter of 3.1 to 3.3 with a coil wire diameter of 250 micrometers, a coil length of 250 micrometers and a pitch of about 2.0 mm and may have been etched. The nonconductive adhesive 17 is epoxy resin adhesive setting in a period of 10 minutes.

In order to reduce the driving current, the SMA coil actuator may be reduced in diameter. For example, the SMA coil actuator may have an outer diameter of 0.3 to 0.4 mm and a wire diameter of 100 micrometers or less. The liner coil may have a diameter of 1.3 to 1.5 mm, and the fixing tubes at the forward and rear ends may have a diameter of 0.3 to 0.4 mm. Further more, the nonconductive adhesive should make use of epoxy resin adhesive or the like which is highly heat resistant.

If male and female electrode connectors as shown in FIG. 6 are used, one of them that is used to serve to fix the SMA coil actuator and the liner coil together at their one end may have its one terminal used for grounding the liner coil and the other terminal may be formed as the terminal for conducting current through the SMA coil actuator at its other end. If the liner coil is not grounded, male and female electrode connectors may be formed with a wiring arranged to fix the SMA coil actuator and to conduct current thereto.

Figure 12:
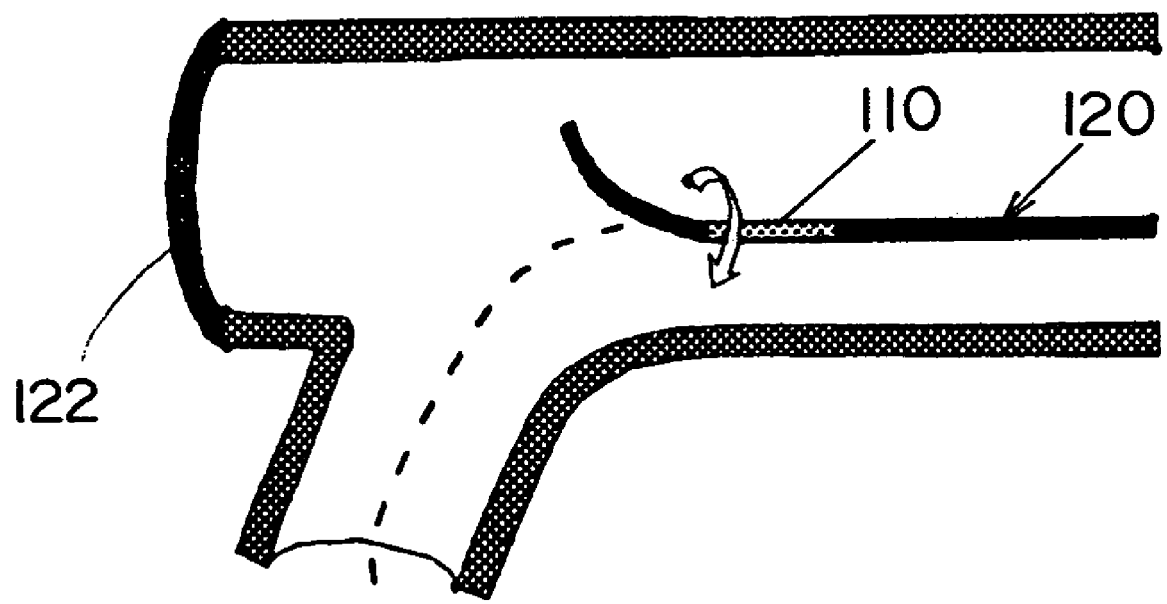
FIG. 12 is a conceptual view that depicts a movement which a torsionally rotating mechanism according to that form of embodiment of the present invention provides.

In the torsionally rotating mechanism 110 for the active guide wire 120 so constructed as described above, the SMA coil actuator 12 if heated with electric current passed therethrough will be deformed, i.e., shrink or torsionally rotate in order to restore its own natural memory shape and will be capable of rotating with precision the active end portion as indicated by the arrow in FIGS. 1 to 3, e.g., even in a blood vessel 122 as shown in FIG. 12 that may have in its midway a loop or complex travel or span. When the heating current is cut off, the liner coil 6 acts as a biasing spring to permit the SMA coil actuator 12 to restore its initial shape and angle.

Consequently, the active guide wire, so constructed as described above, has the ability to produce a toque at its very active end portion to rotate it with precision.

An explanation will next be given of an extending and retracting mechanism.

Figure 13A:
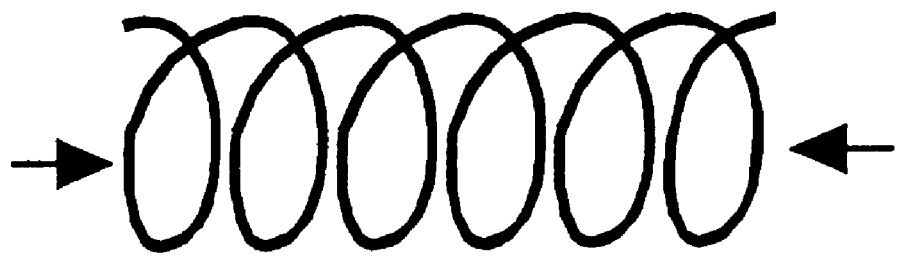
FIG. 13A is a view that depicts a SMA actuator in its shape memory state for an extending and retracting mechanism according to another form of embodiment of the present invention.
Figure 13B:
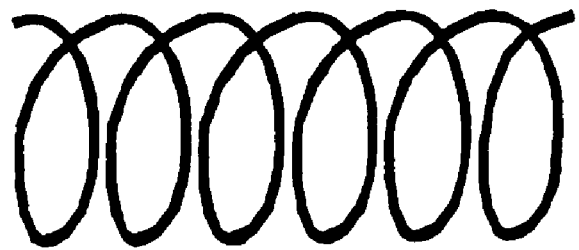
FIG. 13B is a view that depicts the SMA made extending and retracting actuator for that mechanism that is contracted.
Figure 13C:
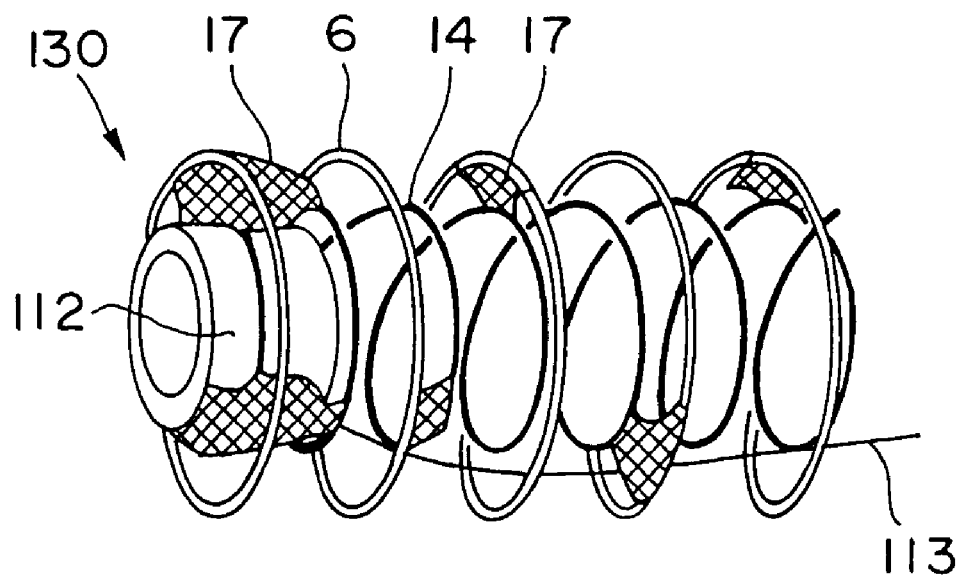
FIG. 13C is an appearance view of an extending and retracting mechanism according to the present invention.

FIGS. 13A, 13B and 13C show an extending and retracting mechanism in more detail with FIG. 13A depicting a SMA coil actuator in its natural shaped memory state, having its natural memory shape or length. FIG. 13B depicts the SMA coil actuator somewhat axially shrunken from its natural memory state. FIG. 13C is a view depicting an appearance of the extending and retracting mechanism.

In forming the extending and retracting mechanism, a biasing element such as served by a liner spring coil may be used that acts to keep the SMA coil actuator normally to be either extended or shrunken, or retracted axially as pulled or compressed, and that acts to allow the SMA coil actuator to be retracted or extended by heating and thereby to restore or to tend to restore its original, natural memory shape or length. The biasing element may be combined with the SMA coil actuator as disposed coaxially therewith to provide an extending and retracting mechanism. Normally, an accurate motion to retract the active, distal end portion of a guide wire or catheter is easily achieved by pulling it at its proximal end portion while the motion to extend the active, distal end portion of the guide wire or catheter is difficult to achieve accurately, as mentioned previously. It is therefore highly desirable to provide a guide wire or catheter in which a motion to extend its active portion is accurately controllable. In order to meet such demands, therefore, the extending and retracting mechanism is here preferably constructed as of the type with the ability to extend its active end portion only upon demand of such an action and to allow it to automatically restore (retract) when the action is ended.

Referring to FIG. 13, the extending and retracting mechanism 130 makes use of a SMA made coil actuator 14 which is disposed inside a liner spring coil 6 and fastened thereto coaxially therewith. Here, the SMA coil actuator 14 when so fastened has been deformed as axially shrunken to have a coil length somewhat reduced from its original, natural, and undeformed shape memory state. A nonconductive adhesive 17 is here again used to the SMA made extending and retracting coil actuator 14 to the liner spring coil 6 at selected sites. The opposite ends of the SMA coil actuator 14 are fastened to those of the liner spring coil 6 on the fixing tubes 112 and 112 with a nonconductive adhesive 17. Thus, in other respects, the SMA made extending and retracting coil actuator 14 is identical in construction to the SMA made torsionally rotating coil actuator 12 except that as fastened to the liner spring coil 6, the former has been shrunken while the latter has been torsionally rotated.

In the extending and retracting mechanism 130 for an active guide wire or catheter so constructed as described above, the SMA coil actuator 14, if heated with electric current passed therethrough will be deformed, i.e., extended in order to restore its natural memory state and will be capable of extending with precision the active end portion of guide wire as indicated by the arrow in FIGS. 1 to 3 and 14. When the heating current is cut off, the liner spring coil 6 acts as a biasing spring to allow the SMA coil actuator 14 to restore its initial length.

Figure 14:
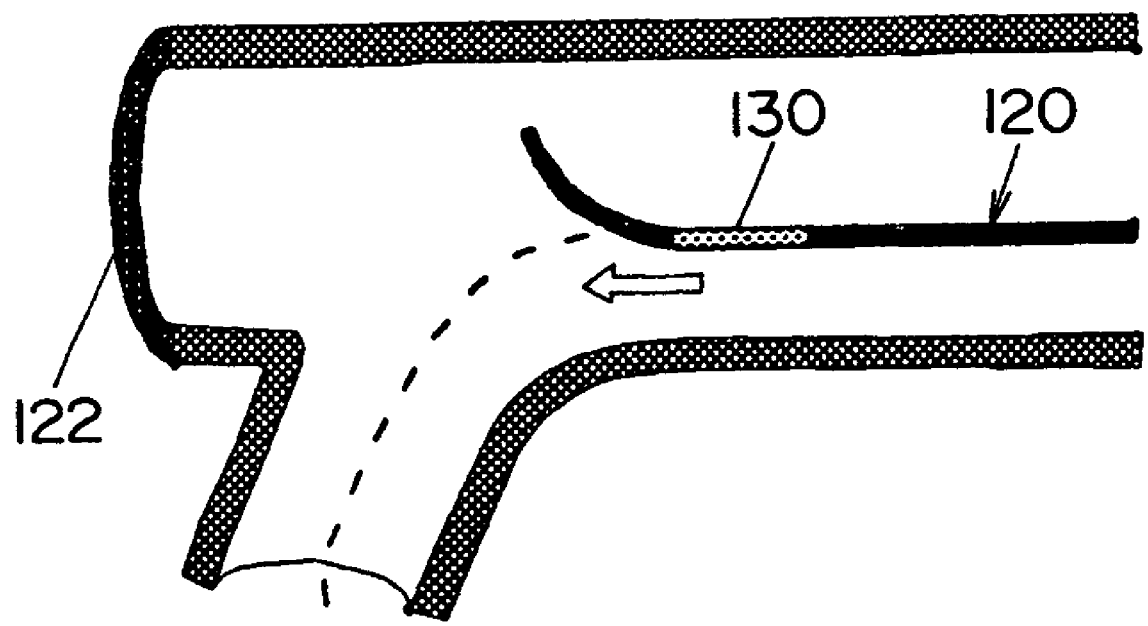
FIG. 14 is a conceptual view that depicts a movement which is provided by an extending and retracting mechanism according to that form of embodiment of the present invention.

Accordingly, the active guide wire or catheter so constructed and functioning as described above has the capability of precisely positioning its active end portion even in a blood vessel 122 as shown in FIG. 14 that may have in its midway a loop or complex travel or span.

An explanation will next be given to a stiffness control mechanism.

Figure 15A:
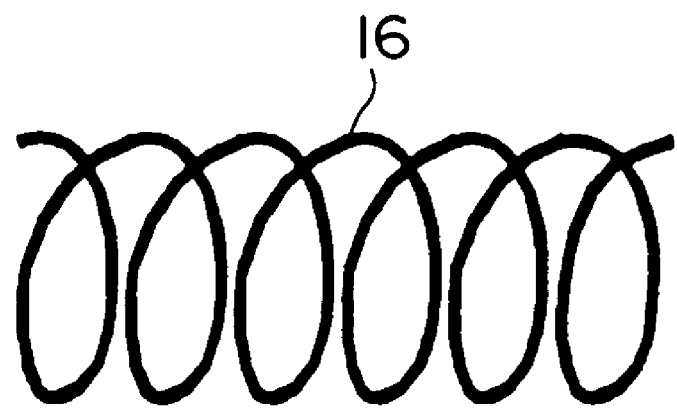
FIGS. 15A and 15B are views that depict a stiffness control mechanism according to another form of embodiment of the present invention with FIG. 15A showing a SMA stiffness control mechanism in its natural shape memory state and FIG. 15B showing an appearance view of the stiffness control mechanism.
Figure 15B:
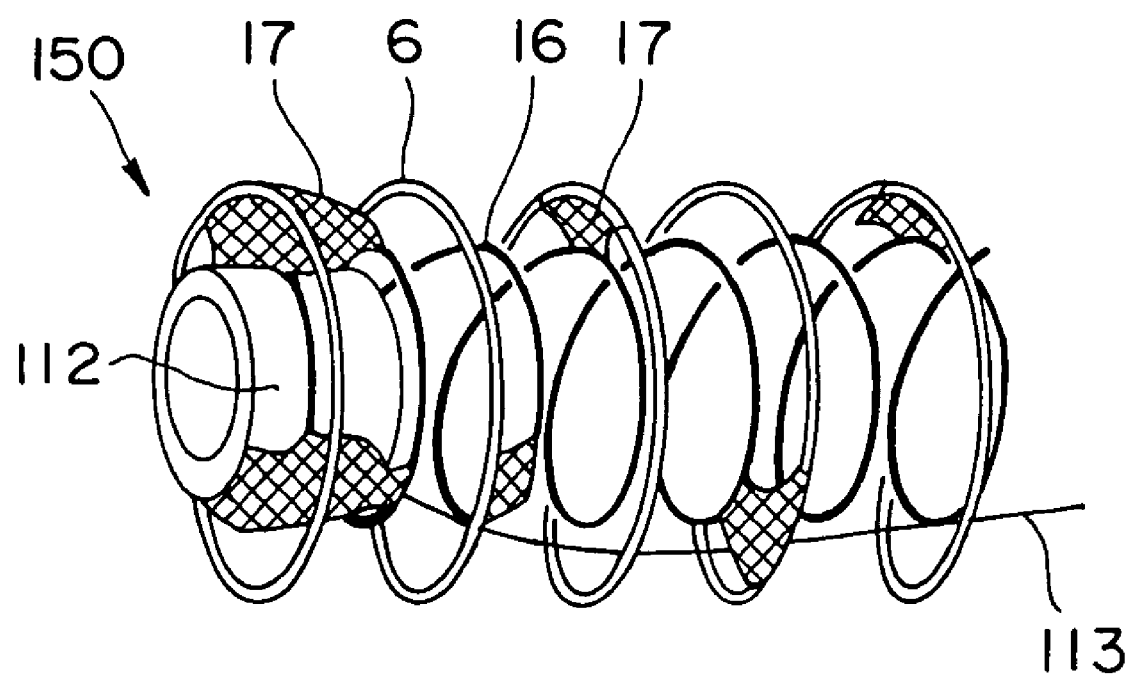

FIG. 15A and FIG. 15B show a stiffness control mechanism in more detail with FIG. 15A depicting a SMA coil actuator in its natural shaped memory state and FIG. 15B being a view that depicts an appearance of the stiffness control mechanism.

Referring to FIGS. 15A and 15B, the stiffness control mechanism denoted by the reference numeral 150 makes use of a SMA made stiffness control coil actuator 16 which is disposed inside a liner coil 6 and fastened thereto coaxially therewith. The SMA made stiffness control coil actuator 16 is thus fastened in its natural memory state. A nonconductive adhesive 17 is used to fasten the SMA made coil actuator 16 to the liner coil 6 at the selected sites. The opposite ends of the SMA coil actuator 16 are fastened to those of the liner coil 6 on the fixing tubes 112 and 112 with a nonconductive adhesive 17. In these and other respects, the SMA made stiffness control coil actuator 16 is identical in construction to the SMA made torsionally rotating coil actuator 12 and the SMA made extending and retracting coil actuator 14 except that although fastened to the liner coil 6, it has not been deformed but has retained its natural shape memory state.

Figure 16A:
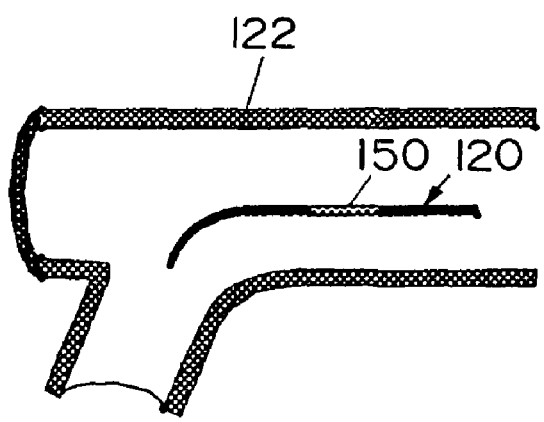
FIGS. 16A and 16B are views that depict movements of the stiffness control mechanism according to that form of embodiment of the present invention.
Figure 16B:
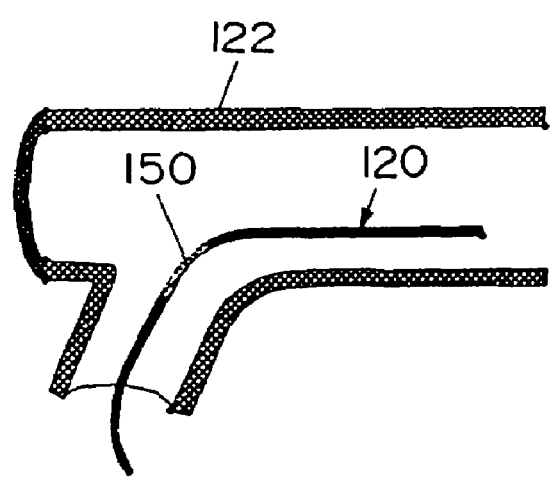
Figure 18F:
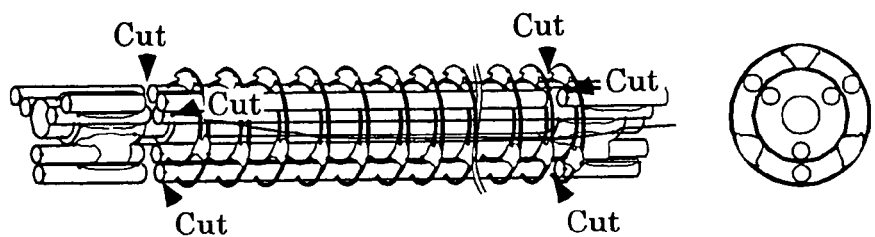
FIGS. 18F and 18G are views that together show a flow chart that indicates how a guide wire of an outer skeleton type can be assembled in another way according to an alternative form of the present invention.
Figure 18G:
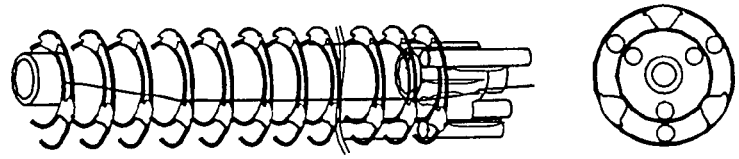

In the stiffness control mechanism 150 as described above, the SMA coil actuator 16, thus the active end portion of a guide wire or catheter, e.g., in a blood vessel 122 as shown in FIG. 16A, if heated with an electric current passed therethrough will have its own spring constant (stiffness) increased and thus become less flexible. As shown in FIG. 16B, when no heating current is passed through the SMA coil actuator 16, the SMA coil actuator is softer, and is more flexible under an external force.

Thus, by varying the magnitude of electric current passed through the SMA coil actuator 16, it is possible to vary and adjust the stiffness and flexibility of the active portion of the guide wire or catheter.

While a SMA material by nature is flexible under an external force, the significance to the stiffness control mechanism incorporated as a part of an active slender tube as described above is to provide the capability of adjusting the desired stiffness of its distal, active end in a body, e.g., a human body from a site outside of the body itself.

An explanation will now be given of the processes of assembling a torsionally rotating mechanism, an extending and retracting mechanism and a stiffness control mechanism. Each of these mechanisms to be assembled here is of an outer skeleton (exoskeletal) configuration in which a liner coil is disposed as an outer skeleton. Processes of assembling or making these mechanisms differ in respect as if fastened to a liner coil, a SMA coil actuator has its natural shape memory state, or needs to have been deformed, i.e., twisted (torsionally deformed) or shrunken (lengthwise deformed).

As an example, the description below is a process of assembling the torsionally rotating mechanism for an active guide wire.

FIGS. 17A–17E and 18F–18G show steps of a process of assembling an active guide wire of exoskeletal type. It should be noted that each of these Figures shows at its right hand side, a diagrammatic cross sectional view of a tubular object being assembled.

First, as shown FIG. 17A a fixing tube 112 is inserted or mounted onto an assembling tube 171 of silicone rubber, and holder members 78 and 78 are inserted onto the tube 171 from its opposite end sides. In the case of a hollow active guide wire, the silicon made assembling tube 171 is used to constitute an inner tube. If an active guide wire should have a connecting wire for centering, the silicon made assembling tube 171 is replaced with a wire that is soft or flexible.

As shown in FIG. 17B, first, e.g., three as shown, assembling metal rods 173 are fixed to the holder or retainer members 78 and 78 with a nonconductive adhesive 17 and are thereafter covered with a SMA coil actuator 176 as shown in FIG. 17C.

Figures 19A, 19B:
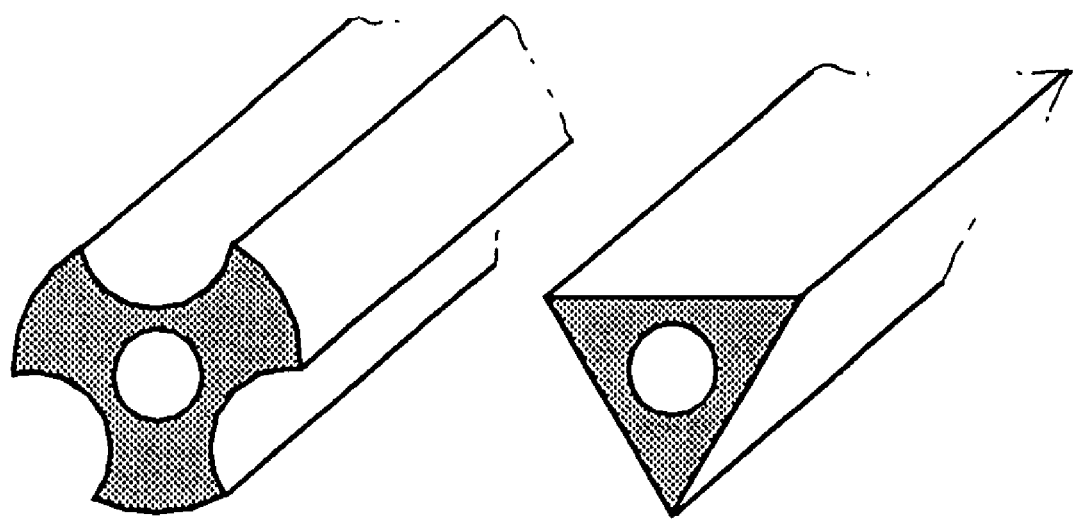
FIGS. 19A and 19B are appearance views that show alternative forms of a jig according to this form of the present invention.

The holder or retainer members 78 and the metal rods 173 used in these process steps can be replaced by an assembling jig, for example, as shown in FIGS. 19A and 19B. The assembling jig shown in FIG. 19 is in the form of a pipe that is circular or triangular in cross section having three sided recesses or grooves. Such a jig allows the SMA actuator coil to be easily positioned. Using a tubular jig having side recesses or grooves may also prevent adhesive from sticking to the jig structure. As its material, Teflon would be suitable to prevent adhesive, if it happens to come in contact with, from sticking, and is also readily machinable into a slender body.

Next, second, e.g., three, assembling metal rods 175 are fixed with a nonconductive adhesive 17 to the first assembling metal rods on the retainer members as shown in FIG. 17D, and lead wires 113 and 113 are electrically connected to the opposite ends of the SMA coil actuator 176 as shown in FIG. 17E. The SMA coil actuator is then covered with a liner coil 6 and fastened thereto at suitable sites with a nonconductive adhesive 17. If the liner coil is used as a ground in the electric circuit, one end of the SMA coil actuator and one end of the liner coil are electrically connected with each other.

Subsequently, the opposite ends of each of the first metal rods 173 and the second metal rods 175 are cut off by using, e.g., a YAG laser, as shown in FIG. 17F. Then, the first and second metal rods that remain are pulled out, the silicone rubber made assembling tube and one of the holder members 78 are removed to leave an assembly as shown in FIG. 17G, and the assembly is covered with an outer tube to complete the process.

The process described above is described as assembling a single unit of a SMA coil and liner coil, and can be equally applied to assemble a plurality of such units as connected together.

The holder members that may be left to form links can be constituted by electrode connectors that are circular in shape. It is desirable to assemble the mechanisms in a single unit.

Using the electrode connectors permits the mechanisms to be made as modular units each of which can be readily connected to and disassembled from the others.

Thus, preparing modular units having their own mechanisms such as those for bending, torsionally rotating and extending and retracting and having other functions of their own such as with an ultrasonic sensor and a chemical sensor, respectively, provides, for example, an operator the ability to choose necessary modules and combine them to prepare a multi-function catheter or the like, as desired in an operating theater.

An explanation will next be given of an assembling process using a metal electro-plating or resin electro-deposition technique. Such a process step requires the use of a SMA coil actuator that is more slender, e.g., having an external diameter of 1.3 mm.

This assembling process is to effect fastening using metal electroplating or resin electro-deposition. It may substitute the process step of fastening an adhesive described before and may be combined with the other process steps previously mentioned.

This assembling process is exemplified below as applied to make a bending mechanism as previously described.

Using a loosely coiled spring in place of a densely packed coil spring, in the bending mechanism, makes the process step applicable for torsionally rotating, and extending and mechanisms as well.

Figure 20A:
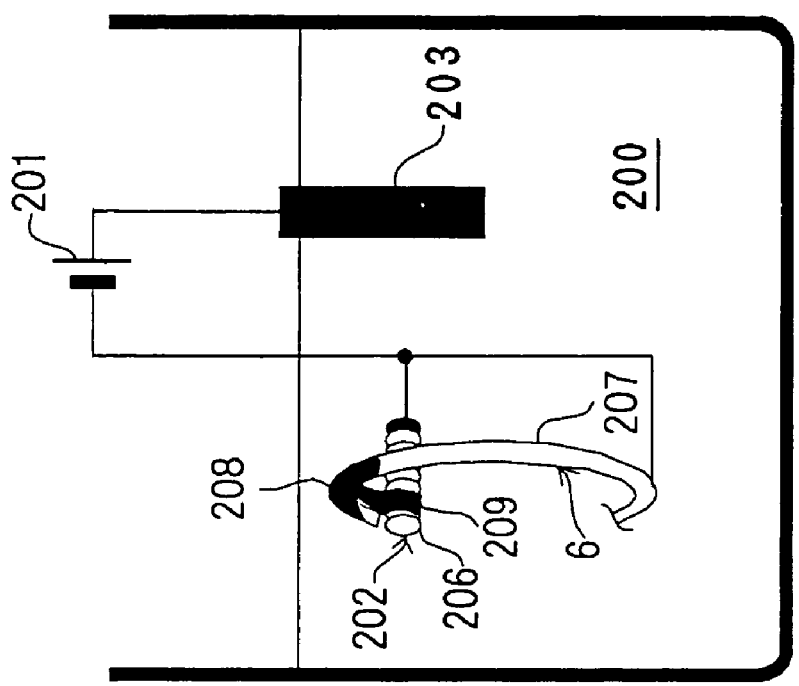
FIGS. 20A and 20B are views that depict essential steps of a process of assembling an active slender tube or tubular object or instrument by electroplating according to another form of embodiment of the present invention and show a pre-electroplating and a post-electroplating stage, respectively.
Figure 20B:
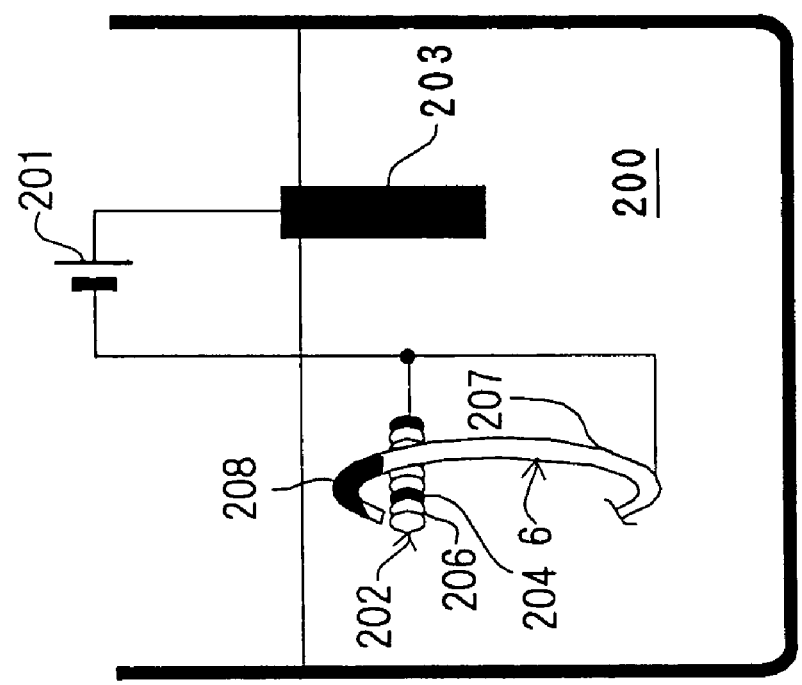

FIGS. 20A and 20B show essential phases of the process of assembling an active slender tube in which the SMA coil actuator and the liner coil are both mechanically fastened and electrically connected together, namely before and after electroplating, respectively.

First, an insulating layer previously coated on the surface of each, a SMA coil actuator 202 and a liner coil spring 6 is ablated locally by using, e.g., a YAG laser to provide non-insulated or electrically conductive portions 204, 208 in the insulating layers. YAG lasers with ablation conditions optimized permit the insulating coating to be ablated in an area as small as several tens micrometers.

In preliminarily applying an insulating layer onto each of the SMA coil actuator and the liner coil spring, it is desirable to use vapor deposition of parylene or electro-deposition of a thermo- or ultraviolet-settable acrylic resin.

Figure 21B:
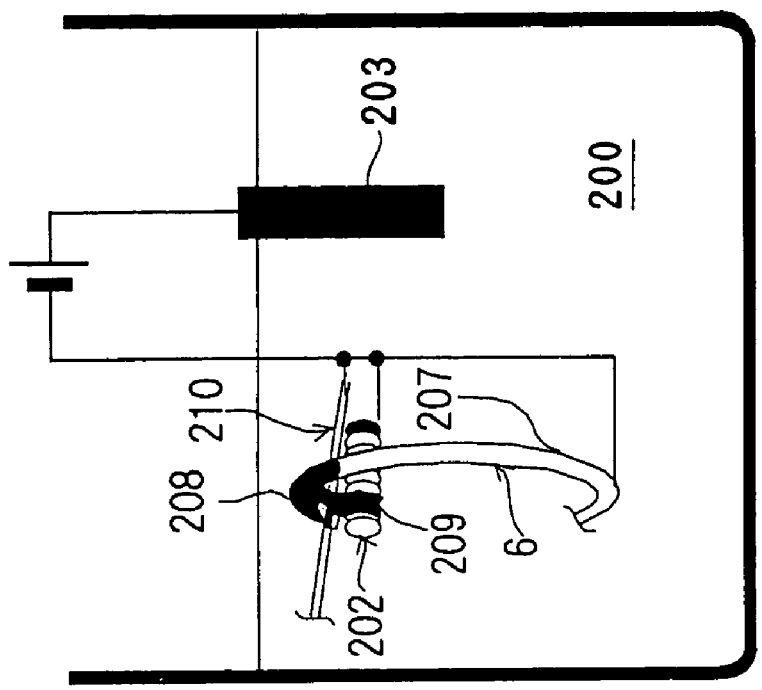
FIGS. 21A and 21B are views that depict essential steps of a process of assembling an active slender tube or tubular object or instrument and a lead wire by electroplating according to an alternative embodiment of the present invention and show a pre-electroplating and a post-electroplating stage, respectively.
Figure 21A:
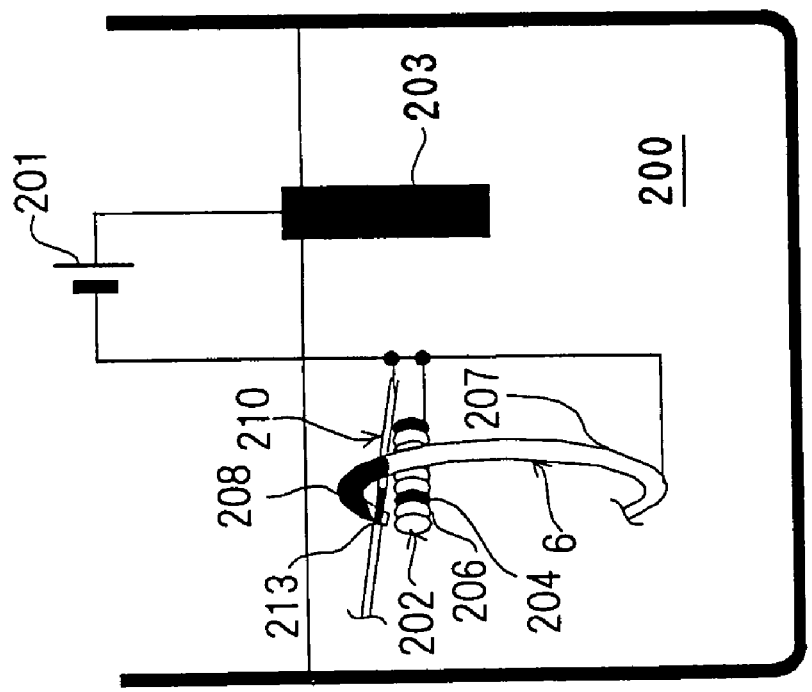

Next, using a jig as shown in FIG. 19A the SMA coil actuator 202 and the liner coil spring 6 are arranged so that the non-insulating portion 204 on the SMA coil actuator 202 and the non-insulating portion 208 on the liner coil 6 may lie close to each other as shown in FIG. 21A. The liner coil 6 and the SMA actuator 202 are immersed in an electroplating solution 200 and are electrically connected to the negative terminal of an essentially DC power supply 201 whose positive terminal is electrically connected and an electrode 203 also immersed in the electroplating liquid 200. The portions of the SMA coil actuator 202 and the liner coil 6 that remain insulated are designated at 206 and 207, respectively.

As shown in FIG. 20B, as an electroplating current is passed from the electrode 203 through the electroplating solution 200 to both the SMA coil actuator 202 and the liner coil 6 a metal, e.g., nickel, is electrolytically deposited from the solution 200 containing the metal onto the non-insulating or conductive portions 204 and 208 on the SMA coil actuator 202 and the liner coil 6 to bond them on those portions. Thus, the SMA coil actuator 202 and the liner coil 6 are both electrically and mechanically connected firmly together at a single site 209 as shown with the deposited metal serving as a bond.

FIGS. 21A and 21B show essential phases of the process of assembling an active slender tube in which the SMA coil actuator, the liner coil and the lead wire are both fastened mechanically and connected electrically by electroplating, by electroplating, namely before and after electroplating, respectively.

As shown in FIG. 21A, if the SMA coil actuator 202, the liner coil 6 and a lead wire 210 are to be connected together, an insulating layer on a lead wire 210 is locally removed to provide a non-insulating or electrically conductive portion 213 thereon. The Lead wire 210, the SMA coil actuator 202 and the liner coil 6 are immersed in the electroplating bath 200 and are arranged so that the non-insulating portions 213, 204 and 208 may lie close to one another.

As an electroplating current supplied from the current source 201 is passed from the electrode 203 through the electroplating solution 200 to the SMA coil actuator 202, the liner coil 6 and the lead wire 210, metal 209, e.g., nickel is electrolytically deposited from the solution 200 onto the non-insulating portions 204, 208 and 213 as shown in FIG. 21B to bond those portions with the metal 209, thereby both electrically connecting and mechanically fastening the SMA coil actuator 202, the liner coil 6 and the lead wire 210 together at a single site as shown.

Figure 22B:
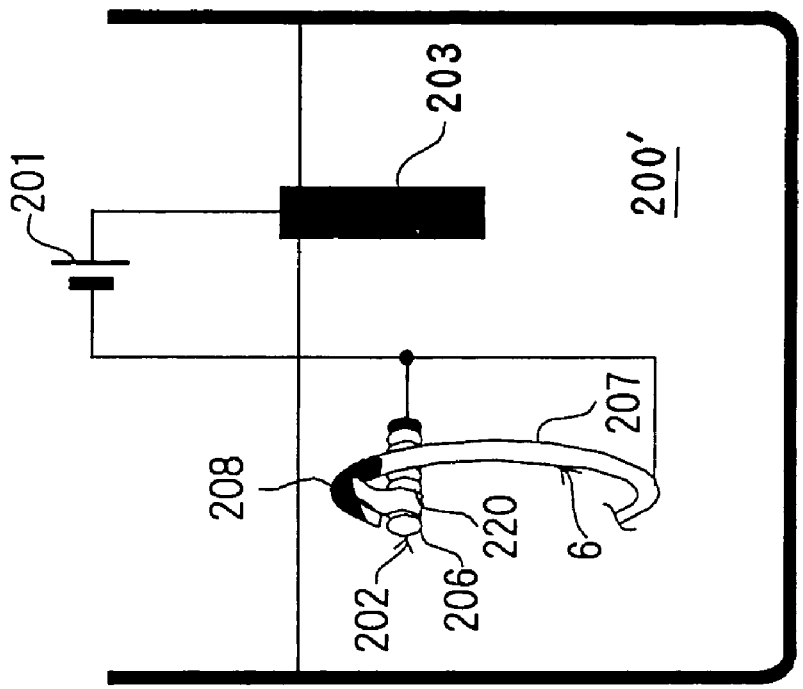
FIGS. 22A and 22B are views that depict essential steps of a process of fastening a liner coil and a SMA actuator together for assembling a slender tube or tubular object or instrument and show a pre-electroplating and a post-electroplating stage, respectively.
Figure 22A:
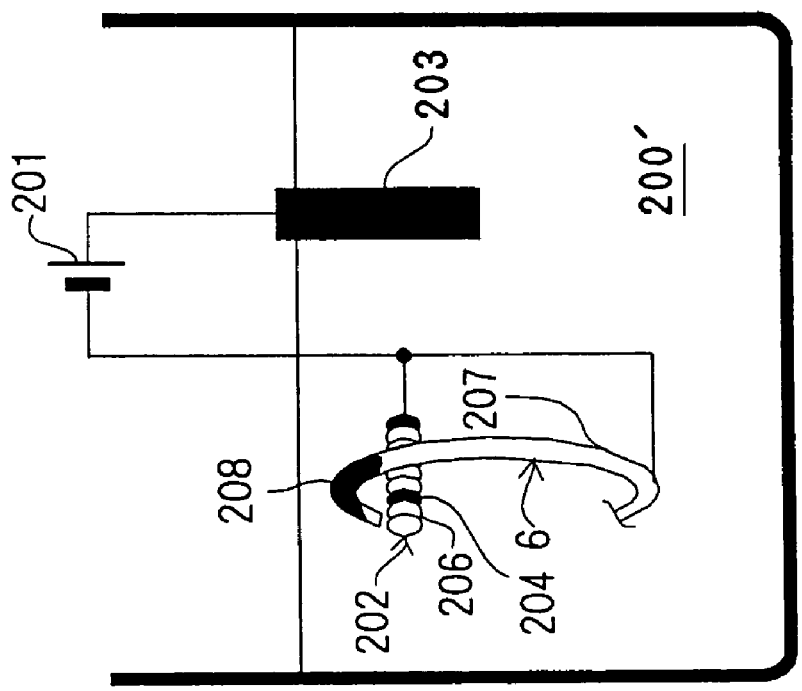

FIGS. 22A and 22B show essential phases of a process of assembling an active slender tube in which the liner coil and the SMA coil actuator are fastened together by electro-deposition of an insulating resin, namely before and after electro-deposition, respectively.

This process replaces the assembling process shown in FIGS. 17 and 18 in which the liner coil and the SMA coil actuator are fastened together by an electrically nonconductive adhesive.

In this process, the electroplating solution in the previous processes is substituted with water in which fine resin particles are dispersed. When an electric potential is applied across the electrode 203 and the non-insulating portions 204 and 208 across the liquid 200', such resin particles positively charged in water migrate in the liquid 200' and are electrophoretically deposited onto the non-insulating portions 204 and 208 of the SMA coil actuator 202 and the liner coil 6 arranged as previously described to bond those portions with the insulator, thereby fastening the SMA actuator and the liner coil locally at a single site as shown.

If, for example, a lead wire is to be electrically connected in an insulating relationship with the liner coil, the metal may be deposited on the non-insulating portions of the lead wire and the SMA actuator from the electroplating solution, and thereafter the insulator may be deposited onto the lead wire and the liner coil electrophoretically as previously described.

Using such an electroplating and electro-depositing assembling process eliminates the need for the use of an adhesive or adhesives, and may also eliminate the need for manual operations and uncertainties in assembling operations associated with the use of an adhesive or adhesives.

Such a process also permits an insulating layer to be ablated at a plurality of sites to provide a plurality of non-insulating portions, and these electrically conductive portions to be electro-deposited with a metal or resin, and hence improves the productivity of active slender tubes and reduces their cost of manufacture.

An explanation will next be given in detail of a process of making a torsionally rotating mechanism by electro-depositing a metal or a resin.

FIGS. 23A to 23G and 24A to 24H show principal process steps of assembling a slender tube by using metal or resin electro-deposition.

Figure 23A:
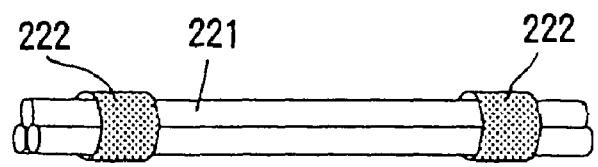
FIGS. 23A to 23G are views that together depict essential steps of a process of fastening a liner coil and a SMA actuator with an insulating resin in assembling a slender tube or tubular object or instrument according to another form of the present invention.

In preparing a torsionally rotating mechanism using metal or resin electro-deposition, for example, three metal rods 221 are passed through heat-shrinkable tubes 222 as shown in FIG. 23A.

Figure 23B:
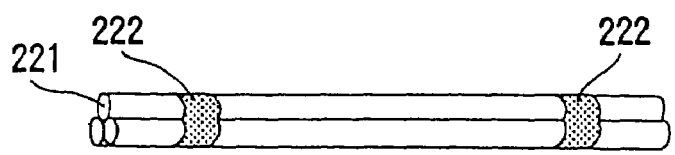
Figure 23C:
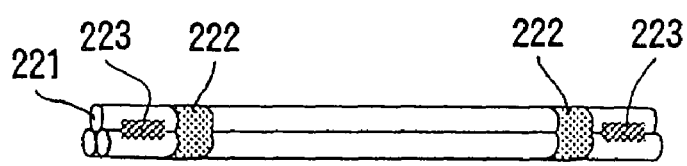
Figure 23D:
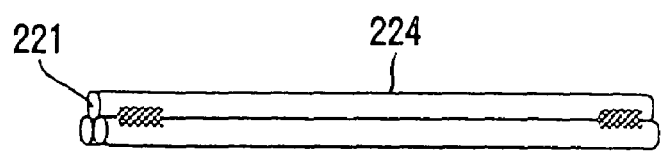

Next, the heat-shrinkable tubes 222 are heated in the step shown in FIG. 23B, and a thermo-settable electrically conductive adhesive 223 is applied onto the end portions of the metal rods 221 as shown in FIG. 23C and allowed to thermally set there. Then, in the step shown in FIG. 23D the heat-shrinkable tubes 222 are removed, and an insulating layer is electro-deposited on the entire surface and hardened.

Figure 23E:
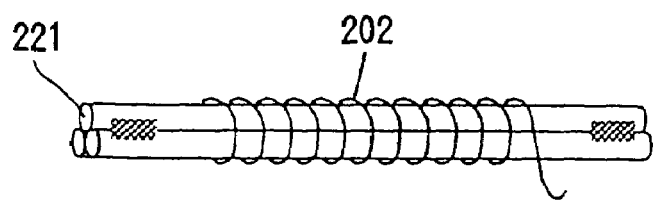
Figure 23F:
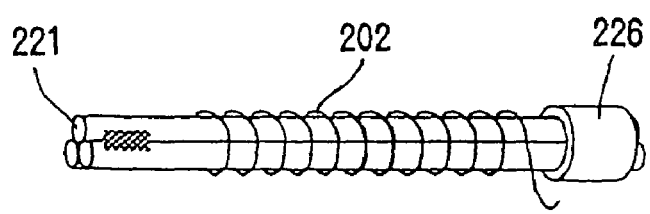
Figure 23G:
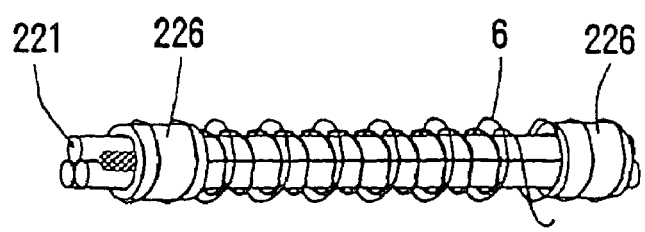

Then, in the step shown in FIG. 23E a wire having an insulating coating preliminarily formed thereon and forming a SMA coil actuator is coiled onto an assembling jig. Then, a silicone rubber made tube 226 is mounted (FIG. 23F), and further the silicone rubber made tube 226 and the liner coil 6 are mounted (FIG. 23G).

Figure 24A:
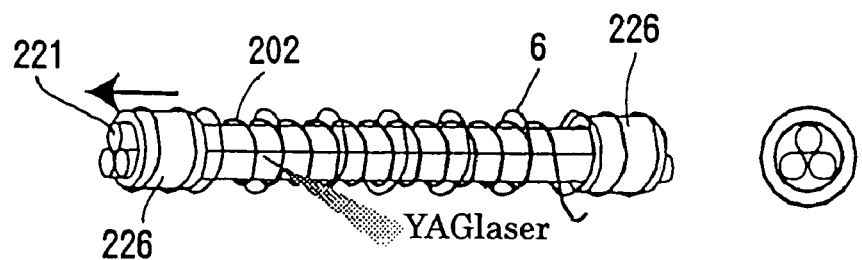
FIGS. 24A to 24H are views that together depict essential steps of an alternative process of fastening a liner coil and an SMA actuator with an insulating resin in assembling a slender tube or tubular object or instrument according to another form of the present invention.

Next, the liner coil 6 is moved as shown in FIG. 24A and the insulating layer on the SMA actuator 202 is locally ablated by a YAG laser to provide a non-insulating portion in the insulating layer.

Figure 24B:
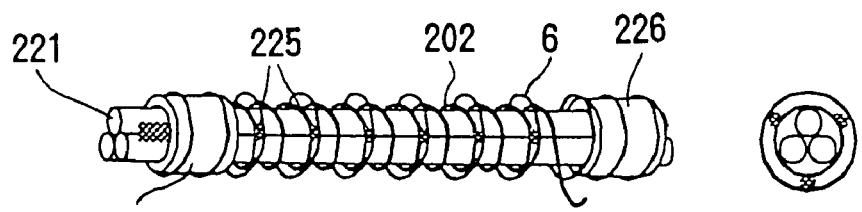

Further, in the step shown in FIG. 24B, the SMA coil actuator 202 immediately prior to the nickel electro-deposition is treated in a dilute fluoric acid solution to remove natural oxide layer thereon. The so treated SMA coil actuator has nickel electroplated thereon to provide an electric connector 225 at its previously formed non-insulating portion.

Figure 24C:
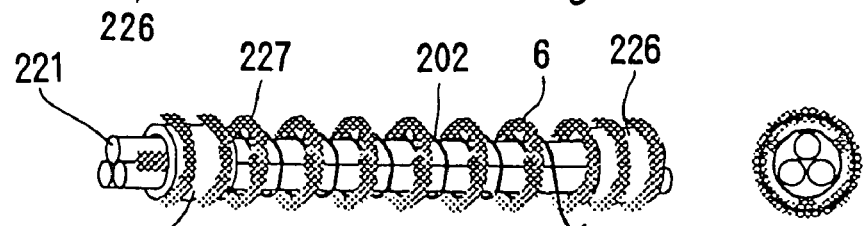

Next, in the step shown in FIG. 24C an acrylic resin 227 is electro-deposited on the electric connector 225 and also on the entire surface of the liner coil 6.

Figure 24D:
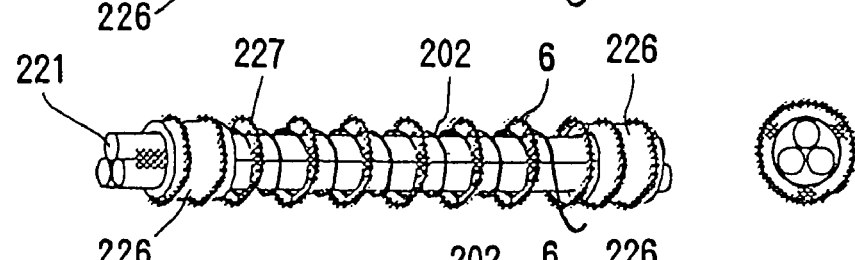

Next, in the step shown in FIG. 24D the acrylic resin coating 227 is dried (dehydrated) by vacuum drying. The dried acrylic coating is polymerized and hardened by ultra-violet irradiation.

Figure 24E:
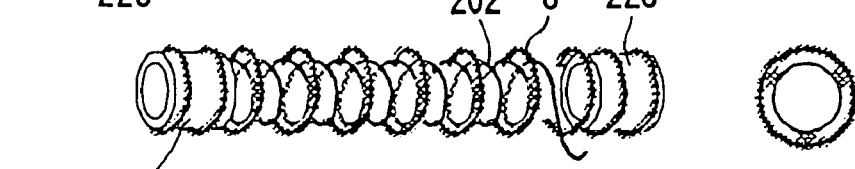

And, in the step shown in FIG. 24E, the assembling metal rods 221 are removed

Figure 24F:
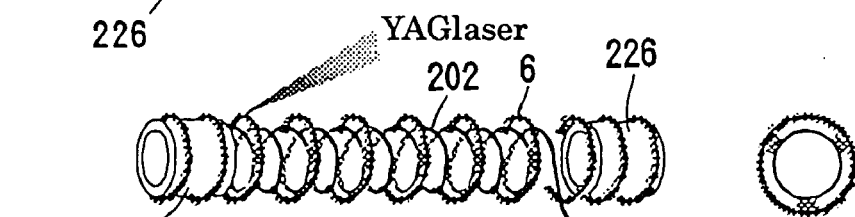

Next, in the step shown in FIG. 24F, the insulating layers on the SMA coil actuator 202 and the liner coil 6 are locally ablated by the YAG laser to provide non-insulating portions thereon.

Figure 24G:
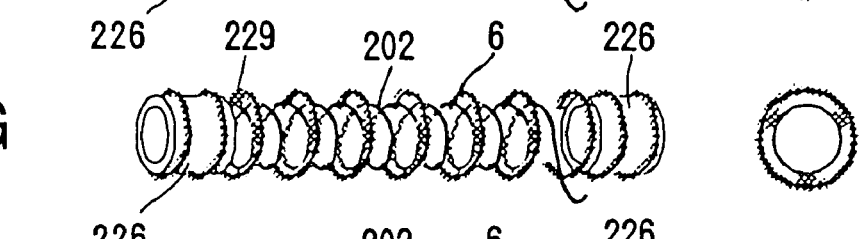

Thereafter, in the step shown in FIG. 24G the SMA coil actuator immediately prior to nickel electroplating is immersed in a dilute fluoric acid solution to remove natural oxide layer 202 thereof and then is electroplated with nickel 229.

Figure 24H:
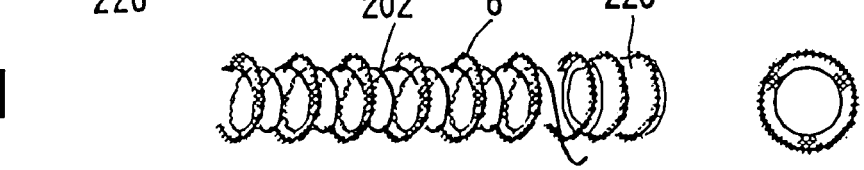

Next, in the step shown in FIG. 24H, the opposite ends are cut off to leave a given length, and the SMA coil actuator 202 and the liner coil are fastened together using resin electro-deposition.

Figure 25A:
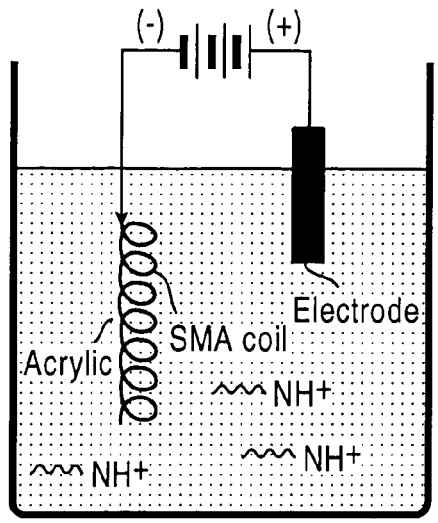
FIGS. 25A, 25B and 25C are diagrammatic views that depict an apparatus construction in a process of electrical metal or resin deposition according to a further form of embodiment of the present invention.

In the process described above, the SMA coil actuator used has acrylic resin preliminarily deposited. To effect such preliminary deposition, the SMA coil actuator connected to an electrode is immersed in a depositing liquid medium as shown FIG. 25A.

Figure 25B:
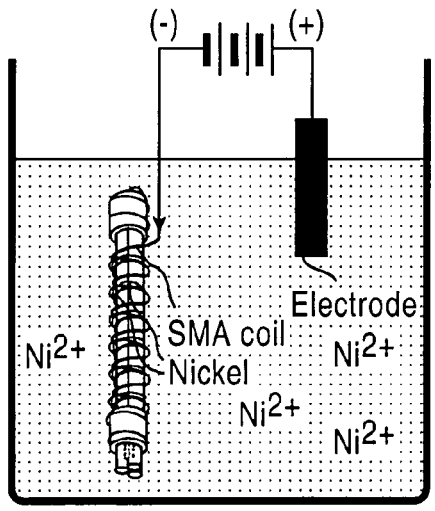
Figure 25C:
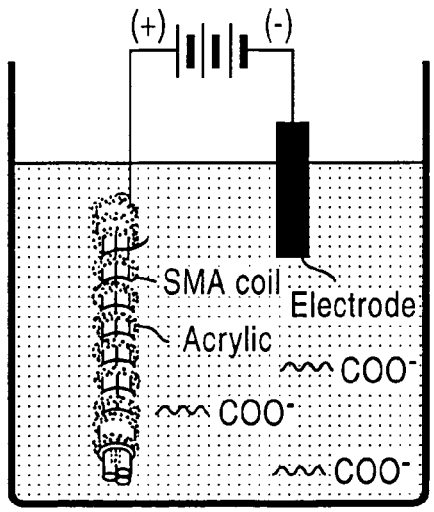

Also, should the SMA coil actuator have metal and the liner coil resin electro-deposited as in the steps shown in FIGS. 24B and 24C, the SMA coil actuator and the liner coil are connected to the electrode in these steps as shown in FIGS. 25B and 25C, respectively.

Such an electric metal plating or a resin deposition process if adopted in the manufacture of an active slender tube herein provided, eliminates the need to use adhesives, is capable of joining the SMA coil and liner coil at a number of sites simultaneously and eliminates uncertainties associated with assembling with adhesives and the need for manual operations.

Also, the ability to make each area of joining smaller permits making an active guide wire with a diameter as small as 0.5 mm or less that could not be assembled using adhesives.

An explanation will next be given of a six form embodiment of the present invention.

Figure 26:
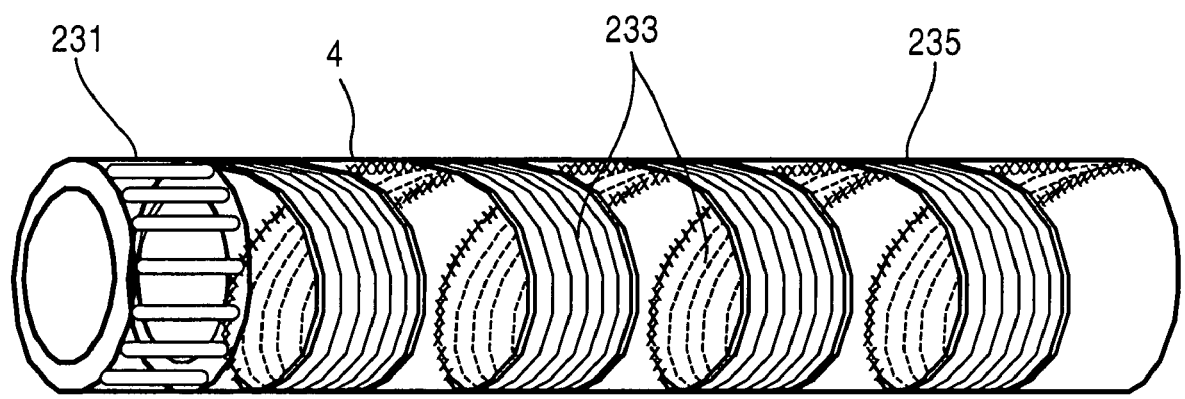
FIG. 26 is a perspective view that illustrates a sixth form of embodiment of the present invention.

FIG. 26 is a perspective view depicting the six forms of embodiment, which permits a number of flexible wirings to be incorporated into a tubular structure such as an active catheter.

Referring to FIG. 26, a spiral shaped board 235 in which a polymeric flat wire spring structure constitutes a wiring board is interposed between a thin outer tube 4 composed of silicone rubber and an inner tube (not shown) to form a tubular object. The object is provided at one of its ends with, e.g., a sensor such as an electrical scanning intra-tubular ultrasonic endoscope. The spiral board has a plurality of metallic wirings 233 arranged and joined as shown (in parallel to one another).

Such a formation permits a plurality of flexible wirings to be incorporated in a tubular structure. Further, stress is not concentrated on any individual wiring and allows the individual wire itself to be made even more slender.

Also, adopting a multi-layer construction made of insulating layers and metallic patterns for the spiral board provides wirings having performance equivalent to those of shield wires and coaxial cables.

Figure 27:
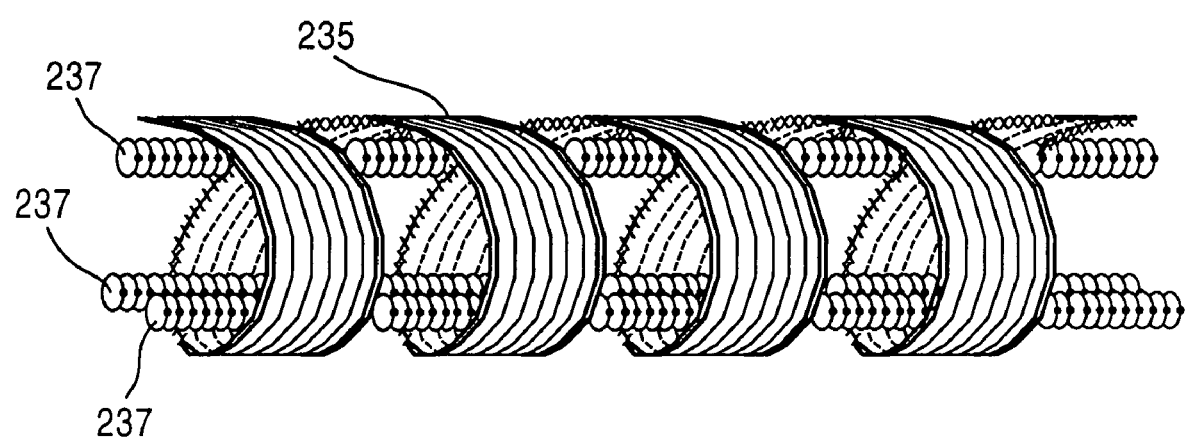
FIG. 27 is an essentially diagrammatic view of an arrangement in which a spiraled cable board is used as a liner coil.

FIG. 27 is a perspective view in part diagrammatic depicting a spiral board used for a liner coil spring.

Using a spiral board 235 that functions by nature as a flat wire spring to provide a liner coil's skeleton structure and fastening it to SMA coil actuators 237 suitably provides an active slender tube such as an active catheter or guide wire.

This form of embodiment permits securing the widest possible working channel in a slender tube while retaining its flexibility.

The spiral board may be disposed to space between a pair of thin silicone rubber made tubes to provide a skeletal structure as with the liner coil. And then, a SMA coil actuator of a flat wire spring structure may be arranged inside those outer tubes skeletonized.

Further, a heater may be disposed on a surface of the SMA coil actuator of a flat wire spring structure with an insulating coating to indirectly heat the SMA coil actuator. Furthermore, the SMA coil actuator of a flat wire spring structure with the insulating coating is provided with an electric wiring or a sensor.

INDUSTRIAL APPLICABILITIES

The advantages offered by a variety of forms of embodiment of an active slender tube according to the present invention include, among others, a simple structure, the ability to be multi-functionalized, i.e., to provide a torsionally rotating, an extending and retracting and/or a stiffness control function and a structure that facilitate the slender tube to be reduced in diameter. An additional advantage that a certain form of the embodiment of the invention is a structural feature that permits a number of flexible wirings to be incorporated. These and other advantages make an active slender tube as implemented as an active catheter or guide wire, any other medical or non-medical micro-mechanical or -system or system's active micro-component highly useful.

Also, advantages offered by a method, embodied in various manners as described, of making an active slender tube according to the present invention include, among others, permitting an active slender tube of a outer skeleton type to be manufactured with precision and efficiently. It if implemented to include a metal electroplating or resin electro-deposition process, offers the advantage of permitting active slender's principal components to be joined or fastened at a plurality or number of sites.

Further, an active slender tube with an exoskeletal configuration according to the present invention permits a SMA coil actuator as a heat emitting element to be located inside a skeletal component is still more advantageously capable of limiting the surface temperature of the active slender tube below a given temperature as required or desired, e.g., if it is implemented as a medical catheter or guide wire, well below 41° C. up to which its use in the human body is permissible.

While the present invention has been described in terms of the presently preferred embodiments thereof, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications fall within the true spirit and scope of the invention.

What is claimed is:

1. A method of making an active slender tube comprising the steps of: preparing an actuator made from a shape memory alloy (SMA) and forming at least a portion of a tubular body; disposing outside of said SMA made actuator an elastically deformable outer skeleton coaxially therewith; and fastening together said SMA made actuator and said outer skeleton, and, characterized in that wherein said step of disposing includes steps of forming non-insulated portions on said SMA made actuator and said outer skeleton in their corresponding areas and disposing a lead wire adjacent to said non-insulated portions, and said step of fastening includes a step of passing an electric current through said lead wire, said SMA made actuator and said outer skeleton in an electroplating liquid to deposit a metal on said lead wire and said non-insulated portions from said liquid and thereby to electrically join said SMA made actuator and said outer skeleton together at said corresponding areas.

2. A method of making an active slender tube comprising the steps of: preparing an actuator made from a shape memory alloy (SMA) and forming at least a portion of a tubular body; disposing outside of said SMA made actuator an elastically deformable outer skeleton coaxially therewith; and fastening together said SMA made actuator and said outer skeleton, and, characterized in that wherein said step of disposing includes a step of forming non-insulated portions on said SMA made actuator and said outer skeleton in their corresponding areas, and said step of fastening includes a step of passing an electric current through said SMA made actuator and said outer skeleton in a liquid containing an insulating resin to electro-deposit said insulating resin on said non-insulated portions from said liquid and thereby to join said SMA made actuator and said outer skeleton together at said corresponding areas.

3. A method of making an active slender tube comprising the steps of: preparing an actuator made from a shape memory alloy (SMA) and forming at least a portion of a tubular body; disposing outside of said SMA made actuator an elastically deformable outer skeleton coaxially therewith; and fastening together said SMA made actuator and said outer skeleton, and, characterized in that wherein said step of disposing includes steps of forming a non-insulated portion and said SMA made actuator and electroplating said non-insulated portion to form an electric connector thereat, and said step of fastening includes a step of passing an electric current through said SMA made actuator and said outer skeleton in a liquid containing an insulating resin to electro-deposit said insulating resin on said electric connector and throughout on said outer skeleton from said liquid and thereby to join said SMA made actuator and said outer skeleton together.

4. A method of making an active slender tube as set forth in claim 2, characterized by further steps of forming non-insulated portions on said SMA made actuator and said outer skeleton and passing an electric current through said outer skeleton and passing an electric current through said SMA made actuator and said outer skeleton in an electroplating liquid to deposit a metal on said non-insulated portions from said liquid and thereby to electrically join said SMA made actuator and said outer skeleton together.

5. A method of making an active slender tube as set forth in claim 4, characterized by a further step of removing natural oxide layer on said SMA made actuator and said outer skeleton immediately prior to depositing the metal and/or insulating resin, respectively.

6. A method of making an active slender tube as set forth in claim 4, characterized by a further step of drying by vacuum drying.

7. A method of making an active slender tube as set forth in any one of claims 1 to 6, characterized in that said of disposing includes a step of cladding a rod with said SMA made actuator.

8. A method of making an active slender tube as set forth in any one of claims 1 to 6, characterized in that said step of disposing includes steps of disposing a rod on said SMA made actuator and cladding said rod with said outer skeleton.

9. A method of making an active slender tube as set forth in any one of claims 1 to 6, characterized in that said step of disposing includes a step of cladding a pipe shaped jig that is triangular in cross section with said SMA made actuator.

* * * * *